(12) United States Patent
Yao

(10) Patent No.: US 12,098,380 B2
(45) Date of Patent: Sep. 24, 2024

(54) VERO CELL LINES STABLY EXPRESSING HSV ICP0 PROTEIN

(71) Applicant: THE BRIGHAM AND WOMEN'S HOSPITAL, INC., Boston, MA (US)

(72) Inventor: Feng Yao, Southborough, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 1021 days.

(21) Appl. No.: 16/619,416

(22) PCT Filed: Jun. 5, 2018

(86) PCT No.: PCT/US2018/035977
§ 371 (c)(1),
(2) Date: Dec. 4, 2019

(87) PCT Pub. No.: WO2018/226638
PCT Pub. Date: Dec. 13, 2018

(65) Prior Publication Data
US 2020/0172928 A1    Jun. 4, 2020

Related U.S. Application Data

(60) Provisional application No. 62/515,260, filed on Jun. 5, 2017.

(51) Int. Cl.
| | |
|---|---|
| A61K 39/245 | (2006.01) |
| C07K 14/005 | (2006.01) |
| C12N 5/071 | (2010.01) |
| C12N 5/16 | (2006.01) |
| C12N 7/02 | (2006.01) |
| C12N 15/86 | (2006.01) |

(52) U.S. Cl.
CPC ............ *C12N 15/86* (2013.01); *A61K 39/245* (2013.01); *C07K 14/005* (2013.01); *C12N 5/0686* (2013.01); *C12N 5/16* (2013.01); *C12N 7/025* (2013.01); *C12N 2710/16622* (2013.01); *C12N 2710/16643* (2013.01); *C12N 2710/16652* (2013.01); *C12N 2830/003* (2013.01); *C12N 2830/60* (2013.01)

(58) Field of Classification Search
None
See application file for complete search history.

(56) References Cited

U.S. PATENT DOCUMENTS

2018/0119111 A1* 5/2018 Delagrave ................ C12N 7/00

FOREIGN PATENT DOCUMENTS

| WO | 2009006618 A2 | 1/2009 |
|---|---|---|
| WO | 2011079073 A2 | 6/2011 |

OTHER PUBLICATIONS

Pellissier et al., Specific tools for targeting and expression in Müller glial cells. Molecular Therapy—Methods & Clinical Development, (2014) 1, 14009 (Year: 2014).*
Khalique, Thesis: Transcriptional Control of ICP0 and Its Effects on Herpes Simplex Virus-1 Replication, 2015, https://repositorio.uam.es/bitstream/handle/10486/667411/khalique_hena.pdf?sequence=1 [retrieved Oct. 17, 2022] (Year: 2015).*
Hena Kalique, PhD thesis (2015), Transcriptional Control of ICP0 and Its Effects on Herpes Simplex Virus-1 Replication, Madrid, Spain (Year: 2015).*
Fukushiga and Sauer, Genomic targeting with a positive-selection lox integration vector allows highly reproducible gene expression in mammalian cells. PNAS (1992), 89: 7905-7909 (Year: 1992).*
Plasmid: pcDNA3.1(+), https://www.addgene.org/vector-database/2093/ [retrieved Feb. 16, 2023] (Year: 2023).*
Ubiquitin E3 ligase ICP0 [Human alphaherpesvirus 1] GenBank: AFE62827.1, https://www.ncbi.nlm.nih.gov/protein/AFE62827.1, published May 10, 2012 [retrieved Feb. 17, 2023] (Year: 2012).*
Clontech, Tet-One™ Inducible Expression System User Manual, published Mar. 23, 2015 (Year: 2015).*
BLAST alignments using tool at https://blast.ncbi.nlm.nih.gov/Blast.cgi (Year: 2023).*
Alberts et al., (2008) Chapter 6: How Cells Read the Genome: From DNA to Protein. Molecular Biology of the Cell, 5th edition. New York, NY: Garland Science. (Year: 2008).*
Hirsch et al., A small regulatory element from chromosome 19 enhances liver specific gene expression. Gene Ther. (2009), 16(1): 43-51 (Year: 2009).*
Vector Builder, Minimal promoters, https://en.vectorbuilder.com/resources/vector-component/minimal-promoter.html, [retrieved Jan. 15, 2024] (Year: 2024).*
Khalique "Transcriptional control of ICP0 and its effect on herpes simplex virus-1 replication." Madrid, Spain 2005—Retrieved from the Internet URL:https://repositorio.uam.es/bitstream/handle/10486/667411/khalique_hena.pdf?sequence=1 [retrieved on Aug. 28, 2018].

* cited by examiner

*Primary Examiner* — Neil P Hammell
*Assistant Examiner* — Catherine Konopka
(74) *Attorney, Agent, or Firm* — Nixon Peabody LLP; David S. Resnick; Jeanne Jodoin

(57) ABSTRACT

Provided herein are Vero cell lines that stably express Herpes Simplex Virus (HSV) ICP0 protein. These cells have the same morphology of Vero cells, exhibit stable expression of HSV ICP0 protein, and also efficiently complement replication of HSV ICP0 deficient virus for greater than 20, 30, or even 40 cell passages.

18 Claims, 3 Drawing Sheets
Specification includes a Sequence Listing.

SEQUENCE LISTING

<160> NUMBER OF SEQ ID NOS: 12

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccattgacgc aaatgggcgg taggcgtgta cggtgggagg tctatataag                50

<210> SEQ ID NO 2
<211> LENGTH: 151
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | | | | |
|---|---|---|---|---|
| atgctaatga | tatacatgcc | acgtacttat | ggtgtctatg | ctaatgatat | tcgcaaatgg | 60 |
| gcggtagacc | ggtgaattca | tgctaatgat | attctttggt | accattgacg | caaatgggcg | 120 |
| gtaggcgtgt | acggtgggag | gtctatataa | g | | | 151 |

<210> SEQ ID NO 3
<211> LENGTH: 3372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | | | | | |
|---|---|---|---|---|---|---|
| atggagcccc | gccccggagc | gagtacccgc | cggcctgagg | gccgccccca | gcgcgaggtg | 60 |
| aggggccggg | cgccatgtct | ggggcgccat | attgggggc | gccatattgg | ggggcgccat | 120 |
| gttgggggac | cccgacccct | tacactggaa | ccggccgcca | tgttggggga | cccccactca | 180 |
| tacacgggag | ccgggcgcca | tgttgggcg | ccatgttagg | gggcgtggaa | cccgtgaca | 240 |
| ctatatatac | agggaccggg | ggcgccatgt | taggggggtgc | ggaacccct | gaccctatat | 300 |
| atacagggac | cggggtcgcc | ctgttggggg | tcgccatgtg | acccctgac | tttatatata | 360 |
| cagaccccca | acacatacac | atggccccctt | tgactcagac | gcagggcccg | gggtcgccgt | 420 |
| gggacccct | gactcataca | cagagacacg | ccccacaac | aaacacacaa | ggaccggggt | 480 |
| cgccgtgttg | ggggcgtggt | ccccactgac | tcatacgcag | ccccccctta | ctcacacgca | 540 |
| tctaggggggg | tggggaggag | ccgcccgcca | tatttgggg | acgccgtggg | accccccgact | 600 |
| ccggtgcgtc | tggagggcgg | gagaagaggg | aagaagaggg | gtcgggatcc | aaaggacgga | 660 |
| cccagaccac | ctttggttgc | agacccctt | ctccccctc | ttccgaggcc | agcagggggg | 720 |
| caggactttg | tgaggcgggg | ggggagagg | gggaactcgt | gggtgctgat | tgacgcggga | 780 |
| aatccccccc | cattcttacc | cgccccccctt | tttcccctt | agcccgcccc | ggatgtctgg | 840 |
| gtgtttccct | gcgaccgaga | cctgccggac | agcagcgact | ctgaggcgga | gaccgaagtg | 900 |
| gggggggcggg | gggacgccga | ccaccatgac | gacgactccg | cctccgaggc | ggacagcacg | 960 |
| gacacggaac | tgttcgagac | ggggctgctg | ggggccgcagg | gcgtggatgg | ggggcggtc | 1020 |
| tcgggggga | gccccccccg | cgaggaagac | ccggcagtt | gcggggcgc | ccccctcga | 1080 |
| gaggacgggg | ggagcgacga | gggcgacgtg | tgcgccgtgt | gcacggatga | gatcgcgccc | 1140 |
| cacctgcgct | gcgacacctt | cccgtgcatg | caccgcttct | gcatcccgtg | catgaaaacc | 1200 |
| tggatgcaat | tgcgcaacac | ctgcccgctg | tgcaacgcca | agctggtgta | cctgatagtg | 1260 |
| ggcgtgacgc | ccagcgggtc | gttcagcacc | atcccgatcg | tgaacgaccc | ccagacccgc | 1320 |
| atggaggccg | aggaggccgt | cagggcgggc | acggccgtgg | actttatctg | gacgggcaat | 1380 |
| cagcggttcg | ccccgcggta | cctgacccctg | ggggggcaca | cggtgagggc | cctgtcgccc | 1440 |
| acccacccgg | agcccaccac | ggacgaggat | gacgacgacc | tggacgacgg | tgaggcgggg | 1500 |
| ggcggcaagg | accctggggg | aggaggagga | ggaggggggg | ggaggagga | ataggcgggc | 1560 |
| gggcgaggaa | agggcgggcc | gggggagggg | cgtaacctga | tcgcgccccc | cgttgtctct | 1620 |
| tgcagcagac | tacgtaccgc | ccgccccccg | ccggacgccc | cgcgccccc | cacgcagagg | 1680 |
| cgccgccgcg | cccccccgtga | cggcggggc | gtctcacgca | gcccccagc | cggccgcggc | 1740 |
| tcggacagcg | ccccccctcgg | cgcccatcgg | gccacacggc | agcagtaaca | ccaacaccac | 1800 |
| caccaacagc | agcggcggcg | gcggctcccg | ccagtcgcga | gccgcggcgc | cgcggggggc | 1860 |

```
gtctggcccc tccggggggg ttggggttgg ggttggggtt gttgaagcgg aggcggggcg    1920
gccgaggggc cggacgggcc cccttgtcaa cagacccgcc cccccttgcaa acaacagaga   1980 ccccatagtg atcagcgact ccccccccggc ctctccccac aggcccccg cggcgcccat    2040 gccaggctcc gccccccgcc ccgggccccc cgcgtccgcg gccgcgtcgg gacccgcgcg    2100 ccccccgcgcg gccgtggccc cgtgcgtgcg agcgccgcct ccggggcccg gccccccgcgc  2160 cccggccccc ggggcggagc cggccgcccg ccccgcggac gcgcgccgtg tgccccagtc    2220
gcactcgtcc ctggctcagg ccgcgaacca agaacagagt ctgtgccggg cgcgtgcgac    2280
ggtggcgcgc ggctcggggg ggccgggcgt ggagggtggg cacggcccct cccgcggcgc    2340 cgcccccctcc ggcgccgccc cgctcccctc cgccgcctct gtcgagcagg aggcggcggt   2400
gcgtccgagg aagaggcgcg ggtcgggcca ggaaaacccc tccccccagt ccacgcgtcc    2460
ccccctcgcg ccggcagggg ccaagagggc ggcgacgcac ccccccctccg actcagggcc   2520 ggggggggcgc ggccagggtg ggcccgggac cccctgacg tcctcggcgg cctccgcctc    2580
ttcctcctct gcctcttcct cctcggcccc gaccccgcg ggggccgcct cttccgccgc     2640
cggggccgcg tcctcctccg cttccgcctc ctcgggcggg gccgtcggtg ccctgggagg    2700
gagacaagag gaaacctccc tcggcccccg cgctgcttct gggccgcggg ggccgaggaa    2760
gtgtgcccgg aagacgcgcc acgcggagac ttccggggcc gtcccgcgg gcggcctcac     2820 gcgctacctg cccatctcgg gggtctctag cgtggtcgcc ctgtcgcctt acgtgaacaa    2880
gactatcacg ggggactgcc tgcccatcct ggacatggag acggggaaca tcggggcgta    2940
cgtggtcctg gtggaccaga cgggaaacat ggcgacccgg ctgcgggccg cggtccccgg    3000
ctggagccgc cgcaccctgc tccccgagac cgcgggtaac cacgtgatgc ccccgagta    3060 cccgacggcc cccgcgtcgg agtggaacag cctctggatg acccccgtgg ggaacatgct    3120
gttcgaccag gcaccctag tgggcgccct ggacttccgc agcctgcggt ctcggcaccc    3180
gtggtccggg gagcaggggg cgtcgacccg ggacgaggga aaacaataac agaacttgtt   3240
tattgcagct tataatggtt acaaataaag caatagcatc acaaatttca caaataaagc    3300
atttttttca ctgcattcta gttgtggttt gtccaaactc atcaatgtat cttatcatgt    3360
ctgaagcttg gc                                                       3372
```

<210> SEQ ID NO 4
<211> LENGTH: 3513
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atgctaatga tatacatgcc acgtacttat ggtgtctatg ctaatgatat tcgcaaatgg    60
gcggtagacc ggtgaattca tgctaatgat attctttggt accattgacg caaatgggcg   120
gtaggcgtgt acgtgggag gtctatataa gcagagctcg tttagtgaac cgtcagatcg     180
cctggagacg ccatccacgc tgttttgacc tccatagaag acaccgggac cgatccagcc    240
tccgcggccg ggaacggtgc attggaacgg actctagagg atccatggag ccccgccccg    300
gagcgagtac ccgccggcct gagggccgcc cccagcgcga ggtgaggggc cgggcgccat    360
gtctggggcc ccatattggg gggcgccata ttgggggcg ccatgttggg gaccccga      420 cccttacact ggaaccggcc gccatgttgg gggacccca ctcatacacg ggagccgggc     480
```

```
gccatgttgg ggcgccatgt tagggggcgt ggaaccccgt gacactatat atacagggac    540
cgggggcgcc atgttagggg gtgcggaacc ccctgaccct atatatacag ggaccggggt    600
cgccctgttg ggggtcgcca tgtgaccccc tgactttata tatacagacc cccaacacat    660
acacatggcc cctttgactc agacgcaggg cccggggtcg ccgtgggacc ccctgactca    720
tacacagaga cacgccccca caacaaacac acaaggaccg gggtcgccgt gttggggggcg    780 tggtccccac tgactcatac gcaggccccc cttactcaca cgcatctagg ggggtgggga    840
ggagccgccc gccatatttg ggggacgccg tgggaccccc gactccggtg cgtctggagg    900
gcgggagaag agggaagaag aggggtcggg atccaaagga cggacccaga ccacctttgg    960
ttgcagaccc ctttctcccc cctcttccga ggccagcagg ggggcaggac tttgtgaggc   1020
ggggggggga gaggggggaac tcgtgggtgc tgattgacgc gggaaatccc ccccccattct   1080 tacccgcccc ccttttttcc ccttagcccg ccccggatgt ctgggtgttt ccctgcgacc   1140
gagacctgcc ggacagcagc gactctgagg cggagaccga agtgggggg cggggggacg   1200 ccgaccacca tgacgacgac tccgcctccg aggcggacag cacggacacg gaactgttcg   1260
agacggggct gctggggccg cagggcgtgg atgggggggc ggtctcgggg gggagccccc   1320
cccgcgagga agaccccggc agttgcgggg gcgccccccc tcgagaggac gggggggagcg   1380 acgagggcga cgtgtgcgcc gtgtgcacgg atgagatcgc gccccacctg cgctgcgaca   1440
ccttcccgtg catgcaccgc ttctgcatcc cgtgcatgaa aacctggatg caattgcgca   1500
acacctgccc gctgtgcaac gccaagctgg tgtacctgat agtgggcgtg acgcccagcg   1560
ggtcgttcag caccatcccg atcgtgaacg accccagac ccgcatggag gccgaggagg   1620
ccgtcagggc gggcacggcc gtggacttta tctggacggg caatcagcgg ttcgccccgc   1680
ggtacctgac cctgggggg cacacggtga gggccctgtc gcccaccac ccggagccca    1740 ccacggacga ggatgacgac gacctggacg acggtgaggc ggggggcggc aaggaccctg   1800
ggggaggagg aggaggaggg ggggggaggg aggaataggc gggcgggcga ggaaagggcg   1860
ggccggggag ggggcgtaac ctgatcgcgc ccccgttgt ctcttgcagc agactacgta   1920
ccgcccgccc ccgccggac gccccgcgcc ccccacgca gaggcgccgc cgcgcccccc    1980
gtgacgggcg gggcgtctca cgcagccccc cagccggccg cggctcggac agcgcccccc   2040
tcggcgccca tcgggccaca cggcagcagt aacaccaaca ccaccaccaa cagcagcggc   2100
ggcggcggct cccgccagtc gcgagccgcg gcgccgcggg gggcgtctgg cccctccggg   2160
ggggttgggg ttggggttgg ggttgttgaa gcggaggcgg ggcggccgag gggccggacg   2220 ggccccctg tcaacagacc cgccccccctt gcaaacaaca gagacccat agtgatcagc   2280 gactccccc cggcctctcc ccacaggccc ccgcgcgc ccatgccagg ctccgccccc    2340 cgcccgggc ccccgcgtc cgcggccgcg tcgggacccg cgcgccccg cgcggccgtg    2400 gccccgtgcg tgcgagcgcc gcctccgggg cccggccccc gcgccccggc ccccggggcg   2460
gagccggccg cccgccccgc ggacgcgcgc cgtgtgcccc agtcgcactc gtccctggct   2520
caggccgcga accaagaaca gagtctgtgc cgggcgcgtg cgacggtggc gcgcggctcg   2580
ggggggccgg gcgtggaggg tgggcacggg ccctcccgcg gcgccgcccc ctccggcgcc   2640
gccccgctcc cctccgccgc ctctgtcgag caggaggcgg cggtgcgtcc gaggaagagg   2700
cgcgggtcgg gccaggaaaa cccctccccc cagtccacgc gtccccccct cgcgccggca   2760
ggggccaaga gggcggcgac gcaccccccc tccgactcag gccgggggg gcgcggccag   2820
```

-continued

```
ggtgggcccg ggaccccccct gacgtcctcg gcggcctccg cctcttcctc ctctgcctct    2880
tcctcctcgg ccccgacccc cgcggggggcc gcctcttccg ccgccggggc cgcgtcctcc    2940
tccgcttccg cctcctcggg cggggccgtc ggtgccctgg gagggagaca agaggaaacc    3000
tccctcggcc cccgcgctgc ttctgggccg cgggggccga ggaagtgtgc ccggaagacg    3060
cgccacgcgg agacttccgg ggccgtcccc gcgggcggcc tcacgcgcta cctgcccatc    3120
tcggggggtct ctagcgtggt cgccctgtcg ccttacgtga acaagactat cacgggggac    3180
tgcctgccca tcctggacat ggagacgggg aacatcgggg cgtacgtggt cctggtggac    3240
cagacgggaa acatggcgac ccggctgcgg gccgcggtcc ccggctggag ccgccgcacc    3300
ctgctccccg agaccgcggg taaccacgtg atgcccccccg agtacccgac ggccccccgcg    3360
tcggagtgga acagcctctg gatgacccccc gtggggaaca tgctgttcga ccagggcacc    3420
ctagtgggcg ccctggactt ccgcagcctg cggtctcggc acccgtggtc cggggagcag    3480
ggggcgtcga cccgggacga gggaaaacaa taa                                 3513
```

<210> SEQ ID NO 5
<211> LENGTH: 776
<212> TYPE: PRT
<213> ORGANISM: Herpes simplex virus 1

<400> SEQUENCE: 5

```
Met Glu Pro Arg Pro Gly Ala Ser Thr Arg Arg Pro Glu Gly Arg Pro
1               5                   10                  15

Gln Arg Glu Pro Ala Pro Asp Val Trp Val Phe Pro Cys Asp Arg Asp
            20                  25                  30

Leu Pro Asp Ser Ser Asp Ser Glu Ala Glu Thr Glu Val Gly Gly Arg
        35                  40                  45

Gly Asp Ala Asp His His Asp Asp Ser Ala Ser Glu Ala Asp Ser
    50                  55                  60

Thr Asp Thr Glu Leu Phe Glu Thr Gly Leu Leu Gly Pro Gln Gly Val
65                  70                  75                  80

Asp Gly Gly Ala Val Ser Gly Gly Ser Pro Pro Arg Glu Glu Asp Pro
                85                  90                  95

Gly Ser Cys Gly Gly Ala Pro Pro Arg Glu Asp Gly Gly Ser Asp Glu
            100                 105                 110

Gly Asp Val Cys Ala Val Cys Thr Asp Glu Ile Ala Pro His Leu Arg
        115                 120                 125

Cys Asp Thr Phe Pro Cys Met His Arg Phe Cys Ile Pro Cys Met Lys
    130                 135                 140

Thr Trp Met Gln Leu Arg Asn Thr Cys Pro Leu Cys Asn Ala Lys Leu
145                 150                 155                 160

Val Tyr Leu Ile Val Gly Val Thr Pro Ser Gly Ser Phe Ser Thr Ile
                165                 170                 175

Pro Ile Val Asn Asp Pro Gln Thr Arg Met Glu Ala Glu Ala Val
            180                 185                 190

Arg Ala Gly Thr Ala Val Asp Phe Ile Trp Thr Gly Asn Gln Arg Phe
        195                 200                 205

Ala Pro Arg Tyr Leu Thr Leu Gly Gly His Thr Val Arg Ala Leu Ser
    210                 215                 220

Pro Thr His Pro Glu Pro Thr Thr Asp Glu Asp Asp Asp Leu Asp
225                 230                 235                 240

Asp Ala Asp Tyr Val Pro Pro Ala Pro Arg Arg Thr Pro Arg Ala Pro
                245                 250                 255
```

Pro Arg Arg Gly Ala Ala Pro Pro Val Thr Gly Ala Ser His
                260                 265             270

Ala Ala Pro Gln Pro Ala Ala Arg Thr Ala Pro Ser Ala Pro
            275             280             285

Ile Gly Pro His Gly Ser Ser Asn Thr Asn Thr Thr Asn Ser Ser
    290                 295             300

Gly Gly Gly Gly Ser Arg Gln Ser Arg Ala Ala Val Pro Arg Gly Ala
305             310             315                 320

Ser Gly Pro Ser Gly Val Gly Val Val Glu Ala Glu Ala Gly Arg
                325             330             335

Pro Arg Gly Arg Thr Gly Pro Leu Val Asn Arg Pro Ala Pro Leu Ala
            340             345             350

Asn Asn Arg Asp Pro Ile Val Ile Ser Asp Ser Pro Ala Ser Pro
            355             360             365

His Arg Pro Pro Ala Ala Pro Met Pro Gly Ser Ala Pro Arg Pro Gly
    370             375             380

Pro Pro Ala Ser Ala Ala Ala Ser Gly Pro Ala Arg Pro Arg Ala Ala
385             390             395                 400

Val Ala Pro Cys Val Arg Ala Pro Pro Gly Pro Gly Pro Arg Ala
                405             410             415

Pro Ala Pro Gly Ala Glu Pro Ala Ala Arg Pro Ala Asp Ala Arg Arg
            420             425             430

Val Pro Gln Ser His Ser Ser Leu Ala Gln Ala Ala Asn Gln Glu Gln
            435             440             445

Ser Leu Cys Arg Ala Arg Ala Thr Val Ala Arg Gly Ser Gly Gly Pro
450             455             460

Gly Val Glu Gly Gly His Gly Pro Ser Arg Gly Ala Ala Pro Ser Gly
465             470             475                 480

Ala Ala Pro Ser Gly Ala Pro Pro Leu Pro Ser Ala Ala Ser Val Glu
            485             490             495

Gln Glu Ala Ala Val Arg Pro Lys Arg Arg Gly Ser Gly Gln Glu
            500             505             510

Asn Pro Ser Pro Gln Ser Thr Arg Pro Pro Leu Ala Pro Ala Gly Ala
            515             520             525

Lys Arg Ala Ala Thr His Pro Pro Ser Asp Ser Gly Pro Gly Gly Arg
530             535             540

Gly Gln Gly Gly Pro Gly Thr Pro Leu Thr Ser Ser Ala Ala Ser Ala
545             550             555                 560

Ser Ser Ser Ser Ala Ser Ser Ser Ala Pro Thr Pro Ala Gly Ala
                565             570             575

Thr Ser Ser Ala Thr Gly Ala Ala Ser Ser Ser Ala Ser Ala Ser Ser
            580             585             590

Gly Gly Ala Val Gly Ala Leu Gly Gly Arg Gln Glu Glu Thr Ser Leu
            595             600             605

Gly Pro Arg Ala Ala Ser Gly Pro Arg Gly Pro Arg Lys Cys Ala Arg
            610             615             620

Lys Thr Arg His Ala Glu Thr Ser Gly Ala Val Pro Ala Gly Gly Leu
625             630             635                 640

Thr Arg Tyr Leu Pro Ile Ser Gly Val Ser Ser Val Ala Leu Ser
                645             650             655

Pro Tyr Val Asn Lys Thr Ile Thr Gly Asp Cys Leu Pro Ile Leu Asp
            660             665             670

Met Glu Thr Gly Asn Ile Gly Ala Tyr Val Val Leu Val Asp Gln Thr
            675                 680                 685

Gly Asn Met Ala Thr Arg Leu Arg Ala Ala Val Pro Gly Trp Ser Arg
690                 695                 700

Arg Thr Leu Leu Pro Glu Thr Ala Gly Asn His Val Thr Pro Pro Glu
705                 710                 715                 720

Tyr Pro Thr Ala Pro Ala Ser Glu Trp Asn Ser Leu Trp Met Thr Pro
                725                 730                 735

Val Gly Asn Met Leu Phe Asp Gln Gly Thr Leu Val Gly Ala Leu Asp
            740                 745                 750

Phe Arg Ser Leu Arg Ser Arg His Pro Trp Ser Gly Glu Gln Gly Ala
755                 760                 765

Ser Thr Arg Asp Glu Gly Lys Gln
770                 775

<210> SEQ ID NO 6
<211> LENGTH: 833
<212> TYPE: PRT
<213> ORGANISM: Herpes simplex virus 2

<400> SEQUENCE: 6

Met Glu Pro Arg Pro Gly Thr Ser Ser Arg Ala Asp Pro Gly Pro Glu
1               5                   10                  15

Arg Pro Pro Arg Gln Thr Pro Gly Thr Pro Ala Ala Pro His Ala Trp
            20                  25                  30

Gly Met Leu Asn Asp Met Gln Trp Leu Ala Ser Ser Asp Ser Glu Glu
        35                  40                  45

Glu Thr Glu Val Gly Ile Ser Asp Asp Leu His Arg Asp Ser Thr
    50                  55                  60

Ser Glu Ala Gly Ser Thr Asp Thr Glu Met Phe Glu Ala Gly Leu Met
65                  70                  75                  80

Asp Ala Ala Thr Pro Pro Ala Arg Pro Pro Ala Glu Arg Gln Gly Ser
                85                  90                  95

Pro Thr Pro Ala Asp Ala Gln Gly Ser Cys Gly Gly Gly Pro Val Gly
            100                 105                 110

Glu Glu Glu Ala Glu Ala Gly Gly Gly Gly Asp Val Cys Ala Val Cys
        115                 120                 125

Thr Asp Glu Ile Ala Pro Pro Leu Arg Cys Gln Ser Phe Pro Cys Leu
    130                 135                 140

His Pro Phe Cys Ile Pro Cys Met Lys Thr Trp Ile Pro Leu Arg Asn
145                 150                 155                 160

Thr Cys Pro Leu Cys Asn Thr Pro Val Ala Tyr Leu Ile Val Gly Val
                165                 170                 175

Thr Ala Ser Gly Ser Phe Ser Thr Ile Pro Ile Val Asn Asp Pro Arg
            180                 185                 190

Thr Arg Val Glu Ala Glu Ala Val Arg Ala Gly Thr Ala Val Asp
    195                 200                 205

Phe Ile Trp Thr Gly Asn Gln Arg Thr Ala Pro Arg Ser Leu Ser Leu
    210                 215                 220

Gly Gly His Thr Val Arg Ala Leu Ser Pro Thr Pro Trp Pro Gly
225                 230                 235                 240

Thr Asp Asp Glu Asp Asp Asp Leu Ala Asp Val Asp Tyr Val Pro Pro
                245                 250                 255

Ala Pro Arg Arg Ala Pro Arg Arg Gly Gly Gly Ala Gly Ala Thr
            260                 265                 270

```
Arg Gly Thr Ser Gln Pro Ala Ala Thr Arg Pro Ala Pro Gly Ala
        275                 280                 285

Pro Arg Ser Ser Ser Gly Gly Ala Pro Leu Arg Ala Gly Val Gly
    290                 295                 300

Ser Gly Ser Gly Gly Pro Ala Val Ala Ala Val Val Pro Arg Val
305                 310                 315                 320

Ala Ser Leu Pro Pro Ala Ala Gly Gly Arg Ala Gln Ala Arg Arg
                325                 330                 335

Val Gly Glu Asp Ala Ala Ala Glu Gly Arg Thr Pro Pro Ala Gly
            340                 345                 350

Gln Pro Arg Ala Ala Gln Glu Pro Pro Ile Val Ile Ser Asp Ser Pro
            355                 360                 365

Pro Pro Ser Pro Arg Arg Pro Ala Gly Pro Gly Pro Leu Ser Phe Phe
    370                 375                 380

Ser Ser Ser Ser Ala Gln Val Ser Ser Gly Pro Gly Gly Gly Gly Leu
385                 390                 395                 400

Pro Gln Ser Ser Gly Arg Ala Ala Arg Pro Arg Ala Ala Val Ala Pro
                405                 410                 415

Arg Val Arg Ser Pro Pro Arg Ala Ala Ala Pro Val Val Ser Ala
                420                 425                 430

Ser Ala Asp Ala Ala Gly Pro Ala Pro Pro Ala Val Pro Val Asp Ala
    435                 440                 445

His Arg Ala Pro Arg Ser Arg Met Thr Gln Ala Gln Thr Asp Thr Gln
    450                 455                 460

Ala Gln Ser Leu Gly Arg Ala Gly Ala Thr Asp Ala Arg Gly Ser Gly
465                 470                 475                 480

Gly Pro Gly Ala Glu Gly Gly Pro Gly Val Pro Arg Gly Thr Asn Thr
                485                 490                 495

Pro Gly Ala Ala Pro His Ala Ala Glu Gly Ala Ala Ala Arg Pro Arg
                500                 505                 510

Lys Arg Arg Gly Ser Asp Ser Gly Pro Ala Ala Ser Ser Ser Ala Ser
    515                 520                 525

Ser Ser Ala Ala Pro Arg Ser Pro Leu Ala Pro Gln Gly Val Gly Ala
    530                 535                 540

Lys Arg Ala Ala Pro Arg Arg Ala Pro Asp Ser Asp Ser Gly Asp Arg
545                 550                 555                 560

Gly His Gly Pro Leu Ala Pro Ala Ser Ala Gly Ala Ala Pro Pro Ser
                565                 570                 575

Ala Ser Pro Ser Ser Gln Ala Ala Val Ala Ala Ala Ala Ser Ser Ser
    580                 585                 590

Ser Ser Ala Ala Ser Ser Ser Ser Ala Ala Ser Ser Ser Ser Ser
    595                 600                 605

Ala Ala Ser Ser Ser Ser Ala Ala Ser Ser Ser Ala Ala Ser
    610                 615                 620

Ser Ser Ser Ser Ser Ser Ala Ser Ser Ser Ala Gly Gly Ala Gly
625                 630                 635                 640

Gly Ser Val Ala Ser Ala Ser Gly Ala Gly Glu Arg Arg Glu Thr Ser
                645                 650                 655

Leu Gly Pro Arg Ala Ala Ala Pro Arg Gly Pro Arg Lys Cys Ala Arg
                660                 665                 670

Lys Thr Arg His Ala Glu Gly Gly Pro Glu Pro Gly Ala Arg Asp Pro
    675                 680                 685
```

```
Ala Pro Gly Leu Thr Arg Tyr Leu Pro Ile Ala Gly Val Ser Ser Val
        690                 695                 700

Val Ala Leu Ala Pro Tyr Val Asn Lys Thr Val Thr Gly Asp Cys Leu
705                 710                 715                 720

Pro Val Leu Asp Met Glu Thr Gly His Ile Gly Ala Tyr Val Val Leu
                725                 730                 735

Val Asp Gln Thr Gly Asn Val Ala Asp Leu Leu Arg Ala Ala Ala Pro
            740                 745                 750

Ala Trp Ser Arg Arg Thr Leu Leu Pro Glu His Ala Arg Asn Cys Val
        755                 760                 765

Arg Pro Pro Asp Tyr Pro Thr Pro Pro Ala Ser Glu Trp Asn Ser Leu
770                 775                 780

Trp Met Thr Pro Val Gly Asn Met Leu Phe Asp Gln Gly Thr Leu Val
785                 790                 795                 800

Gly Ala Leu Asp Phe His Gly Leu Arg Ser Arg His Pro Trp Ser Arg
                805                 810                 815

Glu Gln Gly Ala Pro Ala Pro Ala Gly Asp Ala Pro Ala Gly His Gly
            820                 825                 830

Glu

<210> SEQ ID NO 7
<211> LENGTH: 1836
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaattcacgc gtccgtgcat gctaatgata ttccgcccaa cgaccccgc ccattgacgt      60 caataatgac gtatgttccc atagtaacgc caatagggac tttccattga cgtcaatggg    120
tggactattt acggtaaact gcatgctaat gatattcttt gactcacggg gatttccaag    180
tctccacccc attgacgtca atgggagttt gttttggcac caaaatcaac gggactttcc    240
aaaatgtcgt aacaactccg ccccattgac gcaaatgggc ggtaggcgtg tacggtggga    300
ggtctatata agcagagctc gtttagtgaa ccgtcagatc gcctggagac gccatccacg    360
ctgttttgac ctccatagaa gacaccggga ccgatccagc ctccgtcgcg aggtgagttt    420
ggggacccct tgattgttct tctttttcgc tattgtaaaa ttcatgttat atggaggggg    480
caaagttttc agggtgttgt ttagaatggg aagatgtccc ttgtatcacc atggaccctc    540
atgataattt tgtttctttc actttctact ctgttgacaa ccattgtctc ctcttatttt    600
cttttcattt tctgtaactt tttcgttaaa ctttagcttg catttgtaac gaattttaa    660 attcactttt gttatttgt cagattgtaa gtactttctc taatcacttt tttttcaagg    720
caatcagggt atattatatt gtacttcagc acagttttag agaacaattg ttataattaa    780
atgataaggt agaatatttc tgcatataaa ttctggctgg cgtggaaata ttcttattgg    840
tagaaacaac tacatcctgg tcatcatcct gcctttctct ttatggttac aatgatatac    900
actgtttgag atgaggataa aatactctga gtccaaaccg ggcccctctg ctaaccatgt    960
tcatgccttc ttcttttcc tacagctgga tccgtgttcc aaccacggtc acgcttcggt   1020
ggccaccatg agcagactgg acaagagcaa ggtgatcaac agcgccctgg agctgctgaa   1080
cgaggtgggc atcgagggcc tgaccaccag aaagctggcc cagaagctgg gcgtggagca   1140
gcccaccctg tactggcacg tgaagaacaa gagagccctg ctggacgccc tggccatcga   1200
```

```
gatgctggac agacaccaca cccacttctg cccctggag ggcgagagct ggcaggactt    1260
cctgagaaac aacgccaaga gcttcagatg cgccctgctg agccacagag acggcgccaa    1320
ggtgcacctg gcaccagac ccaccgagaa gcagtacgag accctggaga accagctggc     1380
cttcctgtgc cagcagggct tcagcctgga gaacgccctg tacgccctga cgccgtgggc    1440
ccacttcacc ctgggctgcg tgctggagga ccaggagcac caggtggcca aggaggagag    1500
agagaccccc accaccgaca gcatgccccc cctgctgaga caggccatcg agctgttcga    1560
ccaccagggc gccgagcccg ccttcctgtt cggcctggag ctgatcatct gcggcctgga    1620
gaagcagctg aagtgcgaga gcggcagcta aataggtagg tagtcgaccc gggacgaggg    1680
aaaacaataa cagaacttgt ttattgcagc ttataatggt tacaaataaa gcaatagcat    1740
cacaaatttc acaaataaag catttttttc actgcattct agttgtggtt tgtccaaact    1800
catcaatgta tcttatcatg tctgaagctt ctgcag                              1836
```

<210> SEQ ID NO 8
<211> LENGTH: 630
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
gccaccatga gcagactgga caagagcaag gtgatcaaca gcgccctgga gctgctgaac     60
gaggtgggca tcgagggcct gaccaccaga aagctggccc agaagctggg cgtggagcag    120 cccacccctgt actggcacgt gaagaacaag agagccctgc tggacgccct ggccatcgag   180
atgctggaca gacaccacac ccacttctgc ccctggagg cgagagctg gcaggacttc     240 ctgagaaaca acgccaagag cttcagatgc gccctgctga gccacagaga cggcgccaag    300
gtgcacctgg gcaccagacc caccgagaag cagtacgaga ccctggagaa ccagctggcc    360
ttcctgtgcc agcagggctt cagcctggag aacgccctgt acgccctgag cgccgtgggc    420
cacttcaccc tgggctgcgt gctggaggac caggagcacc aggtggccaa ggaggagaga    480 gagacccca ccaccgacag catgccccc ctgctgagac aggccatcga gctgttcgac      540
caccagggcg ccgagcccgc cttcctgttc ggcctggagc tgatcatctg cggcctggag    600
aagcagctga agtgcgagag cggcagctaa                                      630
```

<210> SEQ ID NO 9
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgctaatga tattccgccc aacgaccccc gcccattgac gtcaataatg acgtatgttc     60
ccatagtaac gccaataggg actttccatt gacgtcaatg ggtggactat ttacggtaaa    120
ctgcatgcta atgatattct ttgactcacg gggatttcca gtctccaccc ccattgacgt    180
caatgggagt ttgttttggc accaaaatca acgggacttt ccaaaatgtc gtaacaactc    240
cgccccattg acgcaaatgg gcggtaggcg tgtacggtgg gaggtctata taagcagagc    300
tcgtttagtg aaccgtcaga tcgcctggag acgccatcca cgctgttttg acctccatag    360
``` aagcaccgg gaccgatcca gcctccg 387

<210> SEQ ID NO 10
<211> LENGTH: 577
<212> TYPE: DNA
<213> ORGANISM: Unknown
<220> FEATURE:
<223> OTHER INFORMATION: Description of Unknown:
    Beta-globin intron sequence

<400> SEQUENCE: 10

```
aggtgagttt ggggacccctt gattgttctt tcttttttcgc tattgtaaaa ttcatgttat    60
atggaggggg caaagttttc agggtgttgt ttagaatggg aagatgtccc ttgtatcacc   120
atggaccctc atgataattt tgtttctttc actttctact ctgttgacaa ccattgtctc   180
ctcttatttt cttttcattt tctgtaactt tttcgttaaa ctttagcttg catttgtaac   240
gaattttaa attcactttt gtttatttgt cagattgtaa gtactttctc taatcacttt   300
tttttcaagg caatcagggt atattatatt gtacttcagc acagttttag agaacaattg   360
ttataattaa atgataaggt agaatatttc tgcatataaa ttctggctgg cgtggaaata   420
ttcttattgg tagaaacaac tacatcctgg tcatcatcct gcctttctct ttatggttac   480
aatgatatac actgtttgag atgaggataa aatactctga gtccaaaccg ggcccctctg   540
ctaaccatgt tcatgccttc ttcttttttcc tacagct                           577
```

<210> SEQ ID NO 11
<211> LENGTH: 669
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 11

```
gtgttccaac cacggtcacg cttcggtggc caccatgagc agactggaca agagcaaggt    60
gatcaacagc gccctggagc tgctgaacga ggtgggcatc gagggcctga ccaccagaaa   120
gctggcccag aagctgggcg tggagcagcc caccctgtac tggcacgtga agaacaagag   180
agccctgctg gacgccctgg ccatcgagat gctggacaga caccacaccc acttctgccc   240
cctggagggc gagagctggc aggacttcct gagaaacaac gccaagagct tcagatgcgc   300
cctgctgagc acagagacg gcgccaaggt gcacctgggc accagaccca ccgagaagca   360
gtacgagacc ctggagaacc agctggcctt cctgtgccag cagggcttca gcctggagaa   420
cgccctgtac gccctgagcg ccgtgggcca cttcaccctg gctgcgtgc tggaggacca   480
ggagcaccag gtggccaagg aggagagaga ccccccacc accgacagca tgccccccct   540
gctgagacag gccatcgagc tgttcgacca ccagggcgcc gagcccgcct tcctgttcgg   600
cctggagctg atcatctgcg gcctggagaa gcagctgaag tgcgagagcg gcagctaaat   660
aggtaggta                                                           669
```

<210> SEQ ID NO 12
<211> LENGTH: 11
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 12
caaatgggcg g                                                              11
```

VERO CELL LINES STABLY EXPRESSING HSV ICP0 PROTEIN

CROSS-REFERENCE TO RELATED APPLICATIONS

This application is a 35 U.S.C. § 371 National Phase Entry Application of International Application No. PCT/US2018/035977 filed Jun. 5, 2018, which designates the U.S. and claims benefit under 35 U.S.C. § 119(e) of U.S. Provisional Application No. 62/515,260 filed Jun. 5, 2017, the contents of which are incorporated herein by reference in their entireties.

GOVERNMENT SUPPORT

This invention was made with government support under AI093738 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 19, 2018, is named 043214-086910-WOPT_SL.txt and is 30,637 bytes in size.

FIELD OF THE INVENTION

Embodiments of the invention are directed to Vero cell lines that stably express Herpes Simplex Virus (HSV) ICP0 protein and to the generation of these cell lines. These cells have the same morphology of Vero cells, exhibit stable expression of HSV ICP0 protein, and also efficiently complement replication of HSV ICP0 deficient virus for greater than 20, 30, or even 40 cell passages.

BACKGROUND OF THE INVENTION

HSV ICP0 is a multi-functional protein that is required for efficient viral replication at a low multiplicity of infection of HSV in cell cultures (Stow and Stow, *J Gen Virol* 67:2571-2585, 1986; Sacks and Schaffer, *J Virol* 61:829-839, 1987; Yao and Schaffer, *J Virol* 69:6249-6258, 1995). It is a potent activator capable of enhancing gene expression in a promoter independent manner (Hagglund and Roizman, *J Virol.* 78:2169-2178, 2004). ICP0 interacts with a variety of cellular proteins and can target multiple cellular factors for proteasome-mediated degradation (Hagglund and Roizman *J Virol* 78:2169-2178, 2004; Liang et al., *PNAS* 102:5838-5843, 2005; Boutell et al., *J Virol* 79:12342-12354, 2005; Lilley et al., FMBO J29:943-955, 2010; Perusina Lanfranca et al., *Cell* 3:438-454, 2014; Conwell et al., *J Virol* 89:220-229, 2015). In vivo, deletion of ICP0 significantly reduces the virus ability to establish latent infection as well as the reactivation of virus from latent infection (David A. Leib et al., *J Virol* 63: 759-768, 1989, Cai et al., *J Virol* 67:7501-7512, 1993; Halford and Schaffer, *J Virol* 75:3240-3249, 2001; Augustinova H et al., *J Virol* 78:5756-5765, 2004). ICP0 plays a fundamental role in counteracting host innate antiviral response to HSV infection. It prevents an IFN-induced nuclear block to viral transcription, down regulates TLR2/TLR9-induced inflammatory cytokine response to viral infection, suppresses TNF-αt mediated activation of NF-κB signaling pathway, and interferes with DNA damage response to viral infection (reviewed in Perusina Lanfranca et al., *Cell* 3:438-454, 2014). Moreover, ICP0 is required for efficient translation of vial mRNA in quiescent cells (Walsh and Mohr, Genes & Dev 18:660-672, 2004).

Using the T-RExTM gene switch technology (Invitrogen Inc., CA) (Yao et al., *Hum Gene Ther* 9:1939-1950) and the dominant-negative mutant polypeptide UL9-C535C of HSV-1 origin of viral replication binding protein UL9, we constructed a novel class of replication-defective HSV-1 recombinants capable of blocking wild-type HSV-1 and HSV-2 infections (dominant-negative) (Yao and Eriksson. *Hum Gene Ther* 10:1811-1818, 1999; *Antiviral Res* 53:127-133, 2002; Lu et al. *J Invest Dermatol* 129:1174-1184, 2009). These non-replicating and dominant-negative HSV-1 recombinant viruses encode 2 copies of UL9-C535C under control of the tetO-bearing HCMV major immediate-early promoter in the HSV-1 ICP0 locus and are replication-competent only in tetracycline repressor-expressing human osteosarcoma cell line U2CEP4R-11, a stable cell line derived from human osteosarcoma U2OS cells. U2OS is a cell line that specifies an activity that can functionally substitute for ICP0 (Yao and Schaffer, 1995, supra) via an unknown mechanism, but in any case such cells are not preferred to manufacture materials for pharmaceutical purposes.

CJ2-gD2 is an HSV-2 ICP0 deletion mutant based non-replicating dominant-negative HSV-2 recombinant virus that we recently constructed, which encodes 2 copies of the gD2 gene at the HSV-2 ICP0 locus driven by the tetO-bearing HSV-1 major immediate-early ICP4 promoter, while gene encoding UL9-C535C is under the control of the tetO-containing hCMV major immediate-early promoter in an opposite orientation of the inserted gD2 gene. While CJ2-gD2 expresses little gD2 in tetR-expressing cells, it expresses gD2 as efficiently as wild-type HSV-2 infection in non tetR-expressing cells. CJ2-gD2 is avirulent and incapable of establishing detectable latent infection following immunization. We have demonstrated that CJ2-gD2 can function as an effective vaccine in protecting mice and guinea pigs against wild-type HSV-2 genital infection and disease (Akhrameyeva et al. *J Virol* 85:5036-5047, 2011; Zhang et al, *PLoS ONE* 9: e101373; U.S. Pat. No. 8,809, 047).

Due to the lack of ICP0 and high-level expression of UL9-C535C, CJ2-gD2 is replication-defective in Vero cells (Akhrameyeva et al. *J Virol* 85:5036-5047, 2011). Vero cell lines that can complement ICP0 deficient HSV have been generated, however the cell lines have exhibited non-parental cell morphology, slow growth, and loss of complementation efficiency with as little as 15 passages, properties that are not amenable to large scale rigorously regulated clinical production. Sacks and Schaffer describe a Vero cell line that stably expresses HSV-1 ICP0 with an HSV-1 DNA fragment encoding ICP0 gene under its own promoter (Sacks and Schaffer, *J Virol* 61, 1987). These cells, named 0-28, efficiently complement the growth of HSV-1 ICP0 deletion mutants (Sacks and Schaffer, *J Virol* 61:829-839, 1987; Cai and Schaffer, *J Virol* 65:4078-4090, 1991; Yao and Schaffer, *J Virol* 69:6249-6258, 1995). However, the morphology of 0-28 cells was quite different from the parental Vero cells and the growth of 0-28 cells was significantly slower than the parental Vero cells (Yao and Schaffer, unpublished observation), indicating that expression of ICP0 could be toxic to the cells. Indeed, several studies have indicated cytotoxic effect of ICP0 and its inhibitory effect on cell cycle progression and cell proliferation (Samaniego et al., *J Virol* 71:4614-4625, 1997; Everett et al., *EMBO J* 18:1526-1538, 1999; Hobbs et al. *J Virol* 73:8245-8255, 1999; Lomonte and Everett, *J Virol* 73:9456-9467, 1999; Guchet D et al., *J Gen Med* 7:1187-1199, 2005). Samaniego et al. established two ICP0-expressing Vero cell lines, named F06 and L7, using an ICP0-expressing plasmid similar to that used for 0-28 cells, where ICP0 is expressed using its own ICP0 promoter. F06 quickly lost its complement efficiency by passage 15. The stability of L7 in complementing growth was not tested and the limiting quantity of ICP0 provided by L7 cells is purported to explain why there is low levels of tk mRNA upon infection with virus (Samaniego et al., *J Virol*, 1997). Similarly, with ICP0-expressing plasmid, pSH that encodes ICP0 under the ICP0 promoter (Cai and Schaffer, 1989, Yao and Schaffer, 1995), we failed to generate a stable ICP0-expressing Vero cell line that can complement HSV-1 ICP0 deletion mutant efficiently.

Vero cells are known to be good substrate for the production of viruses for pharmaceutical purposes, thus it would be advantageous to have a Vero cell line expressing ICP0 that stably expresses the ICP0 protein for multiple passages and that is capable of complementing ICP0 deficient HSV. Such cells would be suitable for large scale clinical manufacturing of HSV virus vaccines. It is also desirable to have a highly stable Vero cell line that can both efficiently complement ICP0 deficient HSV virus, and inhibit expression of mutant forms of HSV genes that are capable of blocking HSV replication, e.g. dominant negative UL9, and immediate-early expressing of HSV late gene products, e.g. gD.

SUMMARY OF THE INVENTION

We have now identified a means to generate Vero cell lines that stably express HSV ICP0 protein and that are efficient at complementing ICP0 deficient HSV viruses over multiple cell passages. These cells lack toxic effects of ICP0 as observed in other methods for generation of such cells. We have also established a Vero cell-derived cell line, named VOR-124, that is highly stable at expressing both tetracycline Repressor (tetR) and ICP0 protein. This cell line is capable of maintaining complementation efficiency of ICP0 deficient HSV after extensive cell passage. We were able to generate VOR-124, as well as other Vero cell lines, by the establishment of a promoter—ICP0 expression system in Vero cells that allows for just enough expression of ICP0 to efficiently complement replication of ICP0 deficient HSV, but not for so much expression that it has detrimental effect on cells, e.g. slow cell growth, morphology changes, cell death, and eventual loss of expression due to ICP0 toxic effects. With use of the minimal promoter we were able to generate a parental Vero cell line (e.g. V0-584) that stably expresses ICP0 and that maintains its' ICP0 complementation efficiency for greater than 20 cell passages (even for over 40 cell passages). Because of the cells stability, we were then further able to modify this cell line to generate a cell line that expresses both ICP0 and tetR (e.g VOR-124). We further demonstrate that CJ2-gD2 as well as its derivative replicate efficiently in VOR-124 cells, maintaining its complementation efficiency for greater than 50 cell passages Thus, VOR-124 cells, and other Vero cell lines made using our promoter system for expression of ICP0 in Vero cells, are useful for pharmacologic large scale production of ICP0 deficient HSV, e.g. CJ2-gD2, or its derivatives.

Accordingly, aspects and embodiments of the invention are based upon the establishment of a promoter system for HSV ICP0 expression in Vero cells which allows for successful generation of Vero cell lines that stably express ICP0 at levels just enough to efficiently complement replication of ICP0 deficient HSV virus, however not so much that there is a detrimental loss of expression or cell death due to the toxic effects of ICP0. Embodiments of the invention are also based on the successful generation of Vero cells expressing ICP0 that further comprises a Tet repressor (tetR) gene. These cells are highly efficient at replicating HSV ICP0 deletion virus which also encodes a mutant form of HSV protein that blocks HSV DNA replication e.g. dominant negative HSV UL9. Each of these cells unexpectedly stably express ICP0 even over 20, over 30, and even over 40 cell passages and also efficiently complement HSV ICP0 deficient virus over extensive cell passaging. Such cells are amenable for use in clinical production of vaccines, e.g. HSV vaccines or HSV ICP0 deletion mutant-based oncolytic viruses for tumor therapy In one aspect of the invention, a Vero cell line is provided that comprises a nucleotide sequence encoding for Herpes Simplex Virus (HSV) ICP0 protein which is operably linked to the HCMV minimal promoter, where the minimal promoter comprises SEQ ID NO: 1. In one embodiment, the promoter further comprises VP16 responsive elements at the 5' end of the minimal promoter, e.g. SEQ ID NO: 2. In one embodiment, the promoter consists essentially of SEQ ID NO: 2.

In certain embodiments, the HSV ICP0 is selected from HSV-1 ICP0, or variant thereof, and HSV-2 ICP0, or variant thereof. In one embodiment the nucleotide sequence encodes HSV-1 ICP0 that comprises the amino acid sequence of SEQ ID NO: 5. In one embodiment, the nucleotide sequence encodes HSV-2 ICP0 that comprises the amino acid sequence of SEQ ID NO: 6.

In certain embodiments, the Vero cell line comprising a nucleotide sequence that encodes for Herpes Simplex Virus (HSV) ICP0 (e.g. a HSV-1 ICP0 protein or a HSV-2 ICP0 protein) operably linked to a promoter, e.g. a promoter comprising SEQ ID NO: 1 or SEQ ID NO: 2, exhibits the same Vero cell morphology as the cell line from which it was derived (i.e. the parental Vero Cell line morphology). In certain embodiments, the cell line is capable of maintaining ICP0 complementation efficiency, e.g. complementation efficiency is substantially the same whether or not the cell line has been passaged 20, 30, 40, or 50 times within 1 or within 2 standard deviations as measured by a viral replication assay, e.g. plaque forming efficiency assay, an ELISA, or another assay known in the art, for greater than 20 cell passages, or for greater than 30 cell passages, or for even for greater than 40 cell passages.

In another aspect of the invention, a Vero cell line is provided that comprises a nucleotide sequence that encodes for Herpes Simplex Virus (HSV) ICP0 protein, wherein the nucleotide sequence comprises SEQ ID NO: 4. In one embodiment, the Vero cell line exhibits the same Vero cell morphology as the cell line from which it was derived (the parental Vero Cell line morphology). In certain embodiments, the Vero cell line is capable of maintaining ICP0 complementation efficiency, e.g. within 1 or within 2 standard deviations as measured by a viral replication assay, e.g. a plaque forming efficiency assay, ELISA, or other assay, for greater than 20 cell passages, or for greater than 30 cell passages, or even for greater than 40 cell passages.

In another aspect of the invention, a Vero cell line is provided that comprises a nucleotide sequence that encodes for a Herpes Simplex Virus (HSV) ICP0 protein, wherein the nucleotide sequence consists essentially of SEQ ID NO: 4. In one embodiment, the cell line exhibits the same cell morphology as the cell line from which it was derived, i.e. Vero cell morphology. In certain embodiments, the cell line is capable of maintaining ICP0 complementation efficiency, e.g, within 1 or within 2 standard deviations as measured by a viral replication assay, e.g. a plaque forming efficiency assay, an ELISA, or another assay known in the art, for greater than 20 cell passages, or for greater than 30 cell passages, or even for greater than 40 cell passages.

In certain embodiments of each of these aspects of the invention, the Vero cell line further comprises an additional nucleic acid that encodes a tetracycline repressor protein (tetR) operably linked to a promoter. In one embodiment, the promoter comprises SEQ ID NO: 9. In certain embodiments, the nucleic acid that encodes a tetracycline repressor protein encodes the amino acid sequence of SEQ ID NO: 11, or variant thereof. In certain embodiments, the nucleic acid that encodes a tetracycline repressor protein (tetR) which is operably linked to a promoter comprises the nucleotide sequence of SEQ ID NO: 7. This sequence includes a beta-globin intron inserted between the promoter and the tetR nucleotide sequence that encodes the tetR protein. In certain embodiments, the nucleic acid that encodes a tetracycline repressor protein (tetR) operably linked to a promoter consists essentially of SEQ ID NO: 7.

In one aspect, the Vero cell line named V0-584 is provided. V0-584, deposited with the American Type Culture Collection on Apr. 20, 2017 on behalf of the Brigham and Woman's Hospital, Inc. of 75 Francis Street Boston, MA and was assigned ATCC accession no. PTA-124106. We note that reference to this deposit should not create any presumption that such material is necessary to satisfy 35 U.S.C. 112 or that deposit in accordance with these regulations is, or was, required.

In one aspect, the Vero cell line named VOR-124 is provided. VOR-124, deposited with the American Type Culture Collection on Apr. 20, 2017 on behalf of the Brigham and Woman's Hospital, Inc. and was assigned ATCC accession no. PTA-124105. Reference to this deposit should not create any presumption that such material is necessary to satisfy 35 U.S.C. 112 or that deposit in accordance with these regulations is, or was, required.

In certain embodiments of each of these aspects, the Vero cell line further comprises a gene encoding antibiotic resistance. Antibiotic resistant genes are well known to those of skill in the art, including e.g. neomycin and the like.

In certain embodiments of each of these aspects, the Vero cell line further comprises an ICP0 deficient virus, e.g. is infected with an ICP0 deficient virus, or comprises components of an ICP0 deficient virus.

In certain embodiments of each of these aspects, the Vero cell line further comprises a nucleic acid encoding a recombinant protein of interest that is operably linked to a promoter.

In another aspect of the invention, a method of using these Vero cell lines to produce a recombinant protein of interest that is operably linked to a promoter is provided. The recombinant protein may be a therapeutic protein, or a protein for use in a vaccine.

In another aspect of the invention, a method of using these Vero cell lines to produce a virus is provided, e.g. an adenovirus or a Herpes Simplex Virus (HSV). In certain embodiments, the virus is a viral vaccine. In some embodiments, the viral vaccine or viral construct is an ICP0 deficient HSV virus.

In another aspect of the invention, a method of using these Vero cell lines to produce recombinant ICP0 deficient Herpes Simplex Virus (HSV) is provided. The method comprises propagating an ICP0 deficient HSV virus in a Vero cell line of any of each of these aspects of the invention. In one embodiment, the method comprises i) infecting the Vero cell line with an ICP0 deficient HSV virus, ii) incubating the cell line in a tissue culture medium; and iii) collecting the ICP0 deficient virus produced by the cell line.

In another aspect of the invention, methods for generating a Vero cell line that stably expresses HSV ICP0 protein and that efficiently complements ICP0 deficient HSV virus for greater than 20 passages (or even greater than, 30 or 40 passages) is provided. The method comprises contacting Vero cells with a nucleic acid that encodes HSV ICP0 (e.g. HSV1 or HSV2 ICP0) operably linked to a promoter, e.g, wherein the promoter comprises SEQ ID NO: 1 or SEQ ID NO: 2, and screening for complementation of HSV ICP0 deficient virus. In one embodiment, the promoter consists essentially of SEQ ID NO: 2. In one embodiment, the method comprises contacting Vero cells with a nucleic acid that comprises SEQ ID NO: 4. In one embodiment, the HSV ICP0 is HSV-1 ICP0, e.g. SEQ ID NO 5, or variant thereof. In one embodiment, the HSV ICP0 is HSV-2 ICP0, e.g. SEQ ID NO 6, or variant thereof. In one embodiment, the method comprises contacting Vero cells with a nucleic acid that consists essentially of SEQ ID NO: 4 and screening for complementation (replication efficiency) of HSV ICP0 deficient virus.

DESCRIPTION

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The practice of embodiments of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Current Protocols in Immunology* (J. E. Coligan et al., eds., 1999, including supplements through 2016); *Current Protocols in Molecular Biology* (F. M. Ausubel et al., eds., 1987, including supplements through 2016); *Short Protocols in Molecular Biology*, F. M. Ausubel et al., eds., fifth edition 2002, including supplements through 2016; *Molecular Cloning: A Laboratory Manual*. third edition (Sambrook and Russel, 2001); PCR: The Polymerase Chain Reaction. (Mullis et al., eds., 1994); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlags gesellschaft mbH, 1993), *Harlow and Lane Using Antibodies: A Laboratory Manual* Cold Spring Harbor Laboratory Press, Cold Spring Harbor, N.Y., 1999; and Beaucage et al. eds., *Current Protocols in Nucleic Acid Chemistry* John Wiley & Sons, Inc., New York, 2000, including supplements through 2016).

As used herein, the term "cell line" refers to a tissue cultured cell that has been cloned and can be represented by a single cell or a cell population propagated from the single cell clone.

As used herein the term "Vero cell line" refers to a cell line derived from the kidney of a normal adult African green monkey. For example, on Mar. 27, 1962, a cell line derived from the kidney of a normal adult African green monkey named CCL-81 was isolated by Y. Yasumura and Y. Kawakita at the Chiba University in Chiba, Japan; ATCC® CCL-81T™ (Manassas, VA 20110 USA). An optional growth medium for a Vero cell line is Sigma's Delbecco's modified Eagle's Medium (Sigma, ST.LOUIS, MO, 63103, USA), Catalog No. D5796. Complete growth medium, is made by adding the following components to the base medium: fetal bovine serum to a final concentration of 10%. Cells are passaged normally, which is by cell dilution at a time when there is about 100% confluence in a tissue culture dish.

Figure 1:
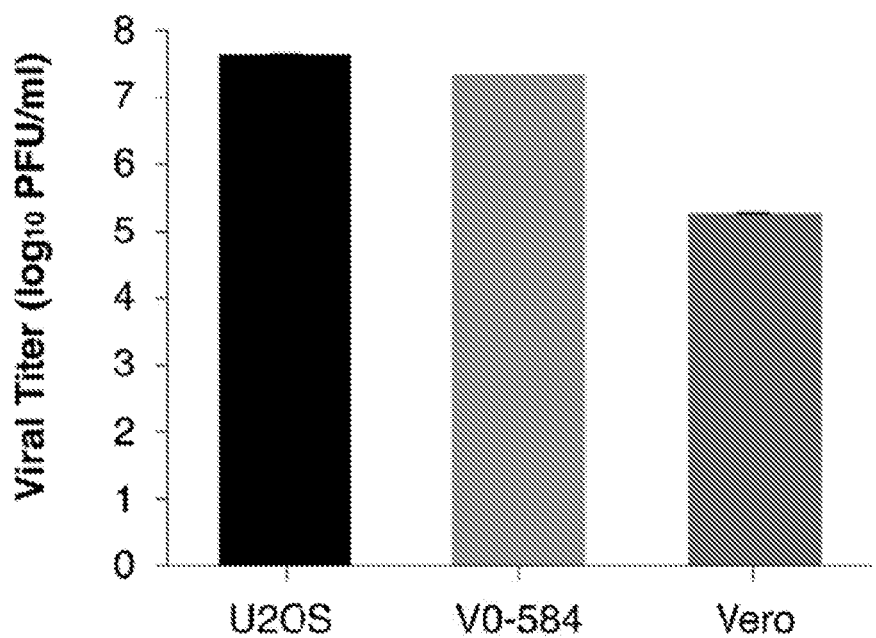
FIG. 1 is a graph that shows plaque-forming efficiency of N2-lacZ, an HSV-2 ICP0 null mutant, in Vero cells, V0-584 cells and U2OS cells. Vero cells and V0-584 cells were seeded at 6×10e5 cells per 60 mm dish and U2OS cells were seeded at $1.25\times10^6$ cells per 60 mm dish. At 46-48 h post-seeding, triplicate dishes of U2OS cells, V0-584 cells, and Vero cells were infected with N2-lacZ at various PFU/dish. After 1.5 h incubation at 37° C. in an inoculation volume of 0.5 ml/dish, methylcellulose was added. Plaques were stained with neutral-red at 72 h post-infection and counted a day later. The number of input PFU was based on the titer on U2OS cell monolayers.
Figure 2:
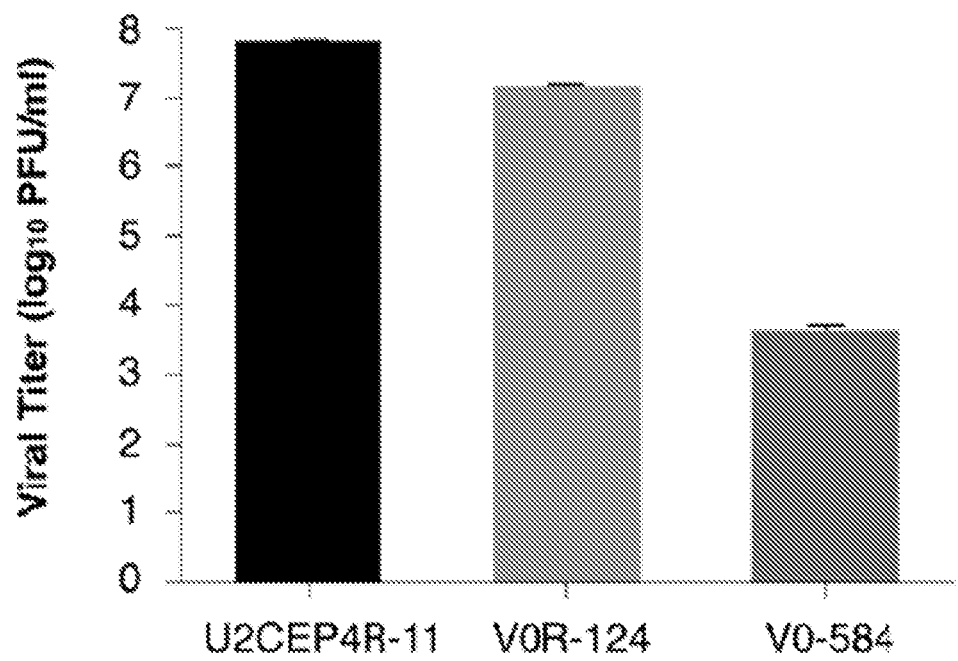
FIG. 2 is a graph that shows the plaque-forming efficiency of CJ2-gD2 in V0-584 cells, VOR-124 cells and U2CEP4R-11 cells. V0-584 cells and VOR-124 were seeded at $6\times10^5$ cells per 60 mm dish and U2CEP4R-11 cells were seeded at $1.25\times10^6$ cells per 60 mm dish. At 46-48 h post-seeding, triplicate dishes of U2CEP4R-11 cells, V0-584 cells and VOR-124 cells were infected with CJ2-gD2 at various PFU/dish. After 1.5 h incubation at 37° C. in an inoculation volume of 0.5 ml/dish, methylcellulose was added. Plaques were stained with neutral-red at 72 h post-infection and counted a day later. The number of input PFU was based on the titer on U2CEP4R-11 cell monolayers.
Figure 3:
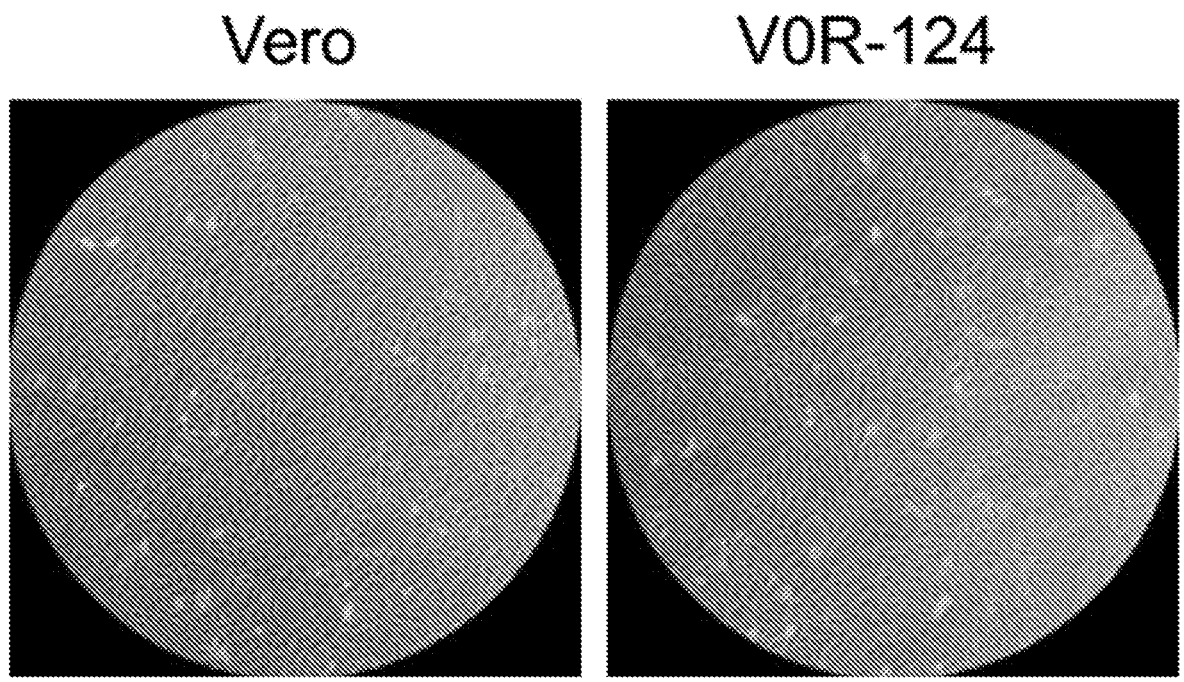
FIG. 3 is a light microscope photograph panel that indicates VOR-124 cells are morphologically similar to Vero cells. Vero cells and VOR-124 cells were seeded at $6\times10^5$ cells per 60 mm dish. Cells were photographed under the light microscope at 48 h post-seeding.
Figure 4:
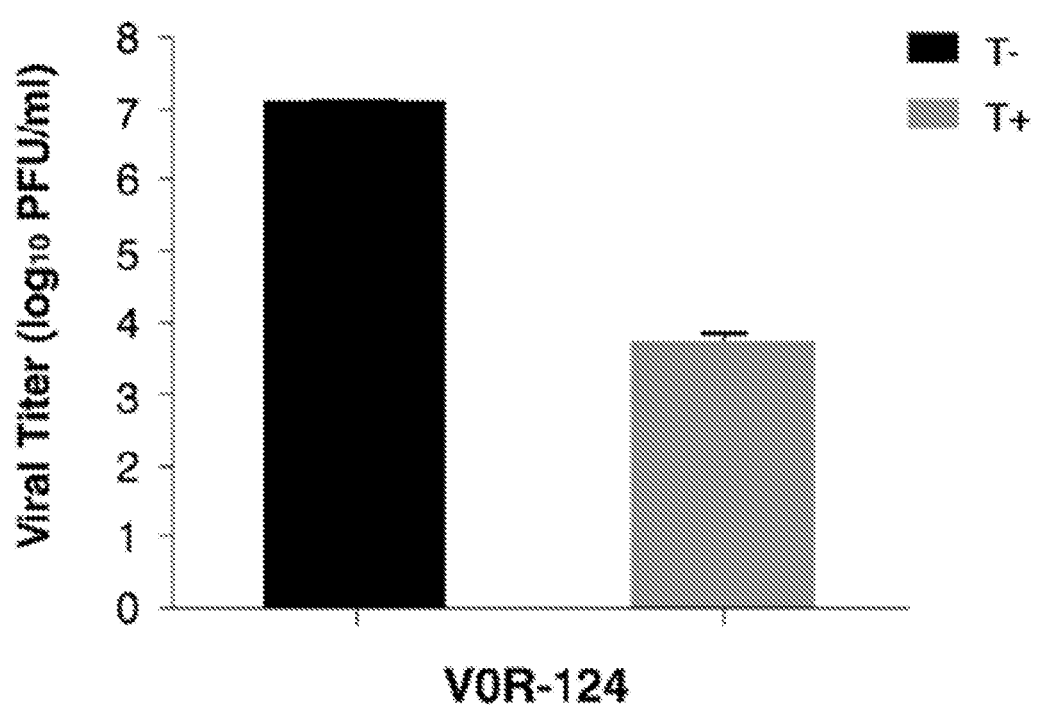
FIG. 4 is a graph of plaque-forming efficiency of CJ2-gD2 in VOR-124 cells in either the absence or presence of tetracycline. VOR-124 were seeded at $6\times10^5$ cells per 60 mm dish. At 45 h post-seeding, triplicate dishes of VOR-124 cells were infected with CJ2-gD2 at 150 PFU/dish for plaque assay in the absence of doxycycline and at $1.5\times10^4$ PFU/dish for plaque-assay in the presence of doxycycline. Plaques were stained with neutral-red at 72 h post-infection and counted a day later. The number of input PFU was based on the titer on VOR-124 cell monolayers.
Figure 5:
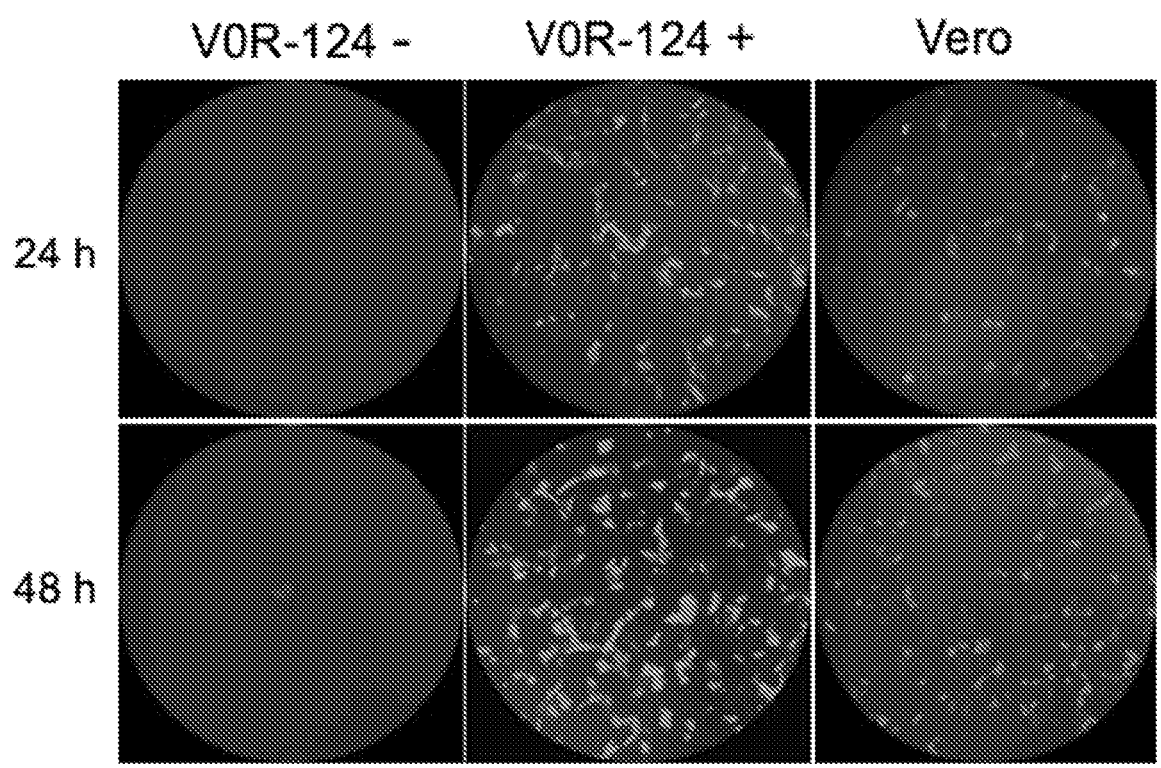
FIG. 5 is a fluorescent microscope photo panel that indicate regulation of eGFP expression from the tetO-containing HCMV major immediate-early promoter in VOR-124 cells in the absence or the presence of doxycycline. VOR-124 cells and Vero cells were seeded at $5 \times 10^5$ cells per 60 mm dish. At 21 h post-seeding, duplicate dishes of VOR-124 cells and Vero cells were transfected with 0.1 ug/dish of pCDNA4TO-eGFP and 1.5 ug/dish of pCDNA3 by Lipofectinamine 2000. Transfection medium was removed at 4 h post-transfection followed by addition of growth medium with or without doxycycline. Expression of EGFP was photographed under the fluorescence microscopy at 24 h and 48 h post-transfection.

As used herein "Vero cell line morphology" refers to the phenotypic shape and membrane structure of a Vero cell which can be determined by microscope (see for example FIG. 3, that shows the morphology of Vero Cells by light microscope).

As used herein the term "herpes simplex virus" (HSV) refers to both HSV type 1 and HSV type 2. See e.g. Fatahzadeh Ml, Schwartz R A. Human herpes simplex virus infections: epidemiology, pathogenesis, symptomatology, diagnosis, and management, *J Am Acad Dermatol,* 2007 November; 57(5):737-63, ATCC holdings (Manassas, VA 20110 USA) include a number of HSV-1 and HSV-2 strains, including for example: HSV-1 HF; HSV-1 MacIntyre; HSV-1 KOS; HSV-1 GHSV-UL46; HSV-1 ATCC-2011-9; HSV-2 MS; HSV-2 G; HSV-2 ATCC-2011-2.

As used herein, the term "ICP0 protein" refers to the HSV protein that is an immediate-early protein which possesses E3 ubiquitin ligase activity. ICP0 activates HSV-1 gene expression, disrupts nuclear domain (ND) 10 structures, mediates the degradation of cellular proteins, and enables evasion of the host's antiviral defenses. As used herein the term "ICP0 deficient HSV" refers to a recombinant HSV vector whose genome does not encode active ICP0 or fully functional ICP0, i.e. ICP0 with normal wild type function. Activity of ICP0 can be monitored using any of the means known to those in the art, See e.g. Miles C Smith et al, HSV-1 ICP0: paving the way for viral replication Future Virol. 2011 April; 6(4): 421-429; Mima P Lanfranca et al., HSV-1 ICP0: An E3 Ubiquitin Ligase that counteracts host intrinsic and immunity, Cells 2014 3:438-454.

There are many variants of HSV ICP0 protein, e.g. some of HSV-1 ICP0, strain KOS variants are: Genebank Accession: P08393.1 GI: 124134; Accession: AFI23590.1 GI: 384597746; Accession: AFI23649.1 GI: 384597805; Accession: AFE62827.1 GI: 380776964; Accession: AFE62886.1 GI: 380777023; Accession: ADM22381.1 GI: 304318198; Accession: ALO18731.1 GI: 952947655; Accession: ALO18672.1 GI: 952947596; Accession: ALO18655.1 GI: 952947578; Accession: ALO18596.1 GI: 952947519; Accession: AKH80472.1 GI: 822581062; Accession: AKH80399.1 GI: 822580988; Accession: AKG61929.1 GI: 820021112; Accession: AKG61857.1 GI: 820021035; etc. and the like. Each strain of HSV1 or of HSV2 have multiple variants, all with functional ICP0. These variants are well known in the art and can be found in protein databases. Such variants may be used in methods of the invention. Examples of HSV-2 ICP0 variants, include but are not limited to: Accession: YP_009137210: YP_009137210.1 GI:820945210; Accession: YP_009137151.1 GI: 820945151; Accession: AEV91397.2 GI: 556197555; Accession: AEV91338.2 GI: 556197550; Accession: ADG01890.1 GI: 295322885; Accession: ADG01889.1 GI: 295322883; Accession: ADG01888.1 GI: 295322881; Accession: ADG01887.1 GI: 295322879; Accession: ADG01885.1 GI: 295322875; Accession: ADG01886.1 GI: 295322877; etc, and the like.

As used herein, the term "variant" or in the context of polypeptides or proteins refers to a polypeptide or protein that comprises an amino acid sequence which has been altered by the introduction of amino acid residue substitutions, deletions and/or additions. Typically substitutions are conservative amino acid substitutions, however non-conservative substitutions can be made that do not destroy the functionality of the protein, e.g. HSV ICP0. "Conservative amino acid substitutions" refers to replacing one amino acid with another having similar structural and/or chemical properties, e.g. such as the replacement of a leucine with an isoleucine or valine, an aspartate with a glutamate, or a threonine with a serine, or glycine with another small amino acid residue. Conservative substitution tables providing functionally similar amino acids are well known in the art. As used herein, the term "non-conservative" refers to substituting an amino acid residue for a different amino acid residue that has different chemical properties. The non-conservative substitutions include, but are not limited to aspartic acid (D) being replaced with glycine (G); asparagine (N) being replaced with lysine (K); or alanine (A) being replaced with arginine (R). For purposes of embodiments of the invention non-conservative substitutions may reduce but does not destroy the proteins normal function.

As used herein the term "comprising" or "comprises" is used in reference to compositions, methods, and respective component(s) thereof, that are essential to the invention, yet open to the inclusion of unspecified elements, whether essential or not.

As used herein the terms, "consisting essentially of," or variations such as "consists essentially of", or "consist essentially of" refer to the inclusion of any recited elements, or group of elements, and the optional inclusion of other elements, of similar or different nature than the recited elements, that do not materially change the basic properties of the claimed elements. For example, a nucleotide sequence that consists essentially of a recited sequence may also include additional one or more nucleic acid additions, deletions, or substitutions that do not materially change by a statistically significant amount the expression level of ICP0 and the ability of the ICP0 protein to complement HSV replication at high efficiency. For example, substitutions may correlate to the degenerative amino acid code.

The term "consisting of" refers to compositions, methods, and respective components thereof as described herein, which are exclusive of any element not recited in that description of the embodiment. For example, the nucleotide sequence has no additions, deletions or substitutions.

As used herein, the terms "protein" are used interchangeably and refer to a polymer or oligomer of consecutive amino acid residues.

As used herein, the terms "nucleotide sequence" refers to DNA molecule sequences (e.g., cDNA or genomic DNA.

As used herein, the term "promoter" refers to regulatory control nucleic acid sequences involved in transcription of nucleotide coding sequences, which may or may not include enhancer elements. Such a promoter may be inducible or constitutive. The term "operably linked" refers to a juxtaposition wherein the components described are in a relationship permitting them to function in their intended manner. A promoter "operably linked" to a coding sequence is ligated in such a way that expression of the coding sequence is achieved.

Other than in the operating examples, or where otherwise indicated, all numbers expressing quantities of ingredients or reaction conditions used herein should be understood as modified in all instances by the term "about." The term "about" when used in connection with percentages may mean±10%, or even e.g. ±20%, preferably ±10%, more preferably ±5%, still more preferably ±1%. In addition, the singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. The abbreviation, "e.g." is derived from the Latin exempli gratia, and is used herein to indicate a non-limiting example. Thus, the abbreviation "e.g." is synonymous with the term "for example."

The term "statistically significant" or "significantly" refers to statistical significance and generally means a two standard deviation (2SD) above or below a normal or reference level. The term refers to statistical evidence that there is a difference. The decision is often made using the p-value. If within two standard deviations than there is not a statistically significant difference.

Embodiments of the invention are based, in part, upon the surprising successful generation of a Vero cell line that encodes ICP0 protein at levels able to complement ICP0 deficient HSV replication at high efficiency, yet at levels that the ICP0 protein remains stably expressed for greater than 20, greater than 30, and even greater than 40 passages. The stability and low toxicity of expression of the ICP0 protein while still being able to complement ICP0 deficient HSV replication at high efficiency (e.g. as evidenced by plaque formation assay) is quite surprising. In particular, we have identified a promoter system that enables the optimal balance of ICP0 expression in Vero cells. The promoter system uses a promoter that comprises SEQ ID NO: 1.

In certain embodiments, the promoter comprises the addition of VP16 responsive elements, e.g. one, two or three VP16 responsive elements, e.g. see SEQ ID NO: 2.

In particular, cell lines can now be produced that complement replication of ICP0 deficient HSV at high efficiency for greater than 20, greater than 30 and even greater than 40 passages.

In embodiments of the invention efficiency of complementation can be determined using any HSV viral replication assay known to those of skill in the art. One such assay is a plaque forming assay also referred to as a plaque forming efficiency assay. HSV plaque assays determine the number of plaque forming units (pfu) in a virus sample, which is one measure of virus quantity and replication, e.g. if measuring the amount of virus produced by a particular Vero cell line. For example, a confluent monolayer of host cells can be infected with HSV ICP0 deficient virus, e.g. produced from a Vero Cell line described herein, at varying dilutions and covered with a semi-solid medium, such as methylcellulose or agar, to prevent the virus infection from spreading indiscriminately. A viral plaque is formed when a virus infects a cell within the fixed cell monolayer. The virus infected cell will lyse and spread the infection to adjacent cells where the infection-to-lysis cycle is repeated. The infected cell area will create a plaque (an area of infection surrounded by uninfected cells) which can be seen by neutral-red staining or with an optical microscope. Plaque formation can take 3-5 days, depending on the virus being analyzed. Plaques are generally counted manually and the results, in combination with the dilution factor used to prepare the plate, are used to calculate the number of plaque forming units per sample unit volume (pfu/mL). The pfu/mL result represents the number of infective particles within the sample and is based on the assumption that each plaque formed is representative of one infective virus particle. Other assays to monitor replication efficiency include but are not limited to, e.g. a focus forming assay (FFA), protein assays, enzyme-linked immunosorbent assay (ELISA), quantitative polymerase chain reaction (qPCR), and flow cytometry, such assays are well known in the art (e.g. Kaufmann, S. H.; Kabelitz, D. (2002). Methods in Microbiology Vol. 32: Immunology of Infection; Martin, S. J. (1978). *The Biochemistry of Viruses*. Cambridge University Press; Flint, S. J.; Enquist,W.; Racaniello, V. R.; Skalka, A. M. (2009). Virological Methods. Principles of Virology. ASM Press). The HSV replication assay (e.g. an assay to determine how much virus is produced by the Vero cell) that is used to determine ICP0 complementation efficiency of an ICP0 expressing Vero cell line described herein, can include a control reference for High efficiency of ICP0 complementation, such as a control cell line, e.g. U2OS or U2CEP4R-11 cells are known to produce infectious virus at concentration (titer) of 7-8 $\log_{10}$ PFU/ml. For comparison the control U2OS cell line value should be seeded to normalize cell number taking inconsideration the growth rates of the cells as to represent the same number of cells producing virus as the tested Vero cell line. As used herein, "high efficiency" refers to having a plaque-forming efficiency for ICP0 null mutants that is equal to, or less than, that observed with U2OS cells, but no more than 10 fold less than that observed with U2OS cells. In one embodiment, the plaque forming efficiency for ICP0 null mutants in the Vero cell line is no more than 5 fold less, or 4 fold less, or 2 fold less, than what is observed with U2OS cells. U2OS cells are available from the American Type Culture Collection (ATCC); (U-2 OS ATCC® HTB96™).

In certain embodiments, the Vero cell line that stably expresses ICP0 has a parental Vero cell morphology. Cell lines may be visualized by light microscopy to assess morphology, see for example FIG. 3. Cell growth kinetics can also be monitored. In one embodiment, the cell growth kinetics of the Vero cell line expressing ICP0 has the same or close to growth kinetics as the parental Vero cells.

In certain embodiments, the HSV ICP0 is selected from HSV-1 ICP0, or variant thereof, and HSV-2 ICP0, or variant thereof. In one embodiment, the nucleotide sequence encodes HSV-1 ICP0, or variant thereof. In one embodiment the nucleotide sequence encodes HSV-1 ICP0 that comprises the amino acid sequence of SEQ ID NO: 5. In one embodiment, the nucleotide sequence encodes HSV-2 ICP0 that comprises the amino acid sequence of SEQ ID NO: 6.

In one aspect, a Vero cell line is provided that comprises a nucleotide sequence that encodes for Herpes Simplex Virus (HSV) ICP0 protein, wherein the nucleotide sequence comprises SEQ ID NO: 4. In one embodiment, the Vero cell line exhibits the same Vero cell morphology as the cell line from which it was derived (the parental Vero Cell line morphology). In certain embodiments, the Vero cell line is capable of maintaining ICP0 complementation efficiency, e.g, within 1 or within 2 standard deviations as measured by plaque forming efficiency assay, for greater than 20 cell passages, or for greater than 30 cell passages, or for even for greater than 40 cell passages.

In one aspect, a Vero cell line is provided that comprises a nucleotide sequence that encodes for a Herpes Simplex Virus (HSV) ICP0 protein e.g. a HSV-1 ICP0 protein or a HSV-2 ICP0 protein, operably linked to a promoter wherein the promoter comprises SEQ ID NO: 2.

In one aspect, a Vero cell line is provided that comprises a nucleotide sequence that encodes for a Herpes Simplex Virus (HSV) ICP0 protein e.g. a HSV-1 ICP0 protein or a HSV-2 ICP0 protein, operably linked to a promoter wherein the promoter consists essentially of SEQ ID NO: 2.

In one aspect, a Vero cell line is provided that comprises the nucleotide sequence of SEQ ID NO: 4, which is a sequence that encodes for a HSV-1 ICP0 protein operably linked to the promoter of SEQ ID NO: 2.

In certain embodiments of each of these aspects, the Vero cell line further comprises an additional nucleic acid that encodes a tetracycline repressor protein (tetR) operably linked to a promoter.

As used herein, a tetracycline repressor protein (tetR) refers to a transcriptional repressor protein that regulates transcription (See e.g Ramos, Juan L et al. (2005-06-01). "the TetR Family of Transcriptional Repressors". Microbiology and Molecular Biology Reviews 69 (2): 326-356, 2005). Many tetR proteins are known in the art and are suitable for use in embodiments of the invention. In one embodiment, the nucleic acid that encodes a tetracycline repressor protein that encodes the amino acid sequence of SEQ ID NO: 11, or variant thereof.

Any promoter known to those of skill in the art may be operably linked to the TetR nucleic acid in embodiments of the invention. In one embodiment, the promoter operably linked to the nucleic acid encoding tetR, comprises SEQ ID NO: 9. In certain embodiments, a beta-globin intron is inserted between the promoter and the tetR nucleotide sequence that encodes the tetR protein (of SEQ ID NO: 7).

In another aspect of the invention, a method of using these Vero cell lines to produce recombinant ICP0 deficient Herpes Simplex Virus (HSV) is provided. The method comprises propagating an ICP0 deficient HSV virus in a Vero cell line of any of each of these aspects of the invention. In one embodiment, the method comprises i) infecting the Vero cell line with an ICP0 deficient HSV virus, ii) incubating the cell line in a tissue culture medium; and iii) collecting the ICP0 deficient virus produced by the cell line. Methods for producing and isolation HSV virus are well known to those of skill in the art, See e.g. Goins W F1, et al. Construction and production of recombinant herpes simplex virus vectors, *Methods Mol Biol.* 2008; 433:97-113; and Herpes Simplex Virus: Propagation, Quantification, and Storage, *Current protocols in microbiology* by John Wiley & Sons, Inc. Chapter 14, 14. E.1-14E.23, contributed by John A. Blaho, Elise R. Morton, and Jamie C. Yedowitz, October 2005). The Vero cell lines described herein use the same medium as suggested for Vero cells.

Methods for generating Vero cell lines that stably expresses HSV ICP0 protein and that efficiently complements ICP0 deficient HSV are also provided. The methods comprise contacting Vero cells with a nucleic acid that encodes HSV ICP0 (e.g. HSV1 or HSV2 ICP0) operably linked to a promoter, e.g. wherein the promoter comprises SEQ ID NO: 1 or SEQ ID NO: 2, and screening for complementation of HSV ICP0 deficient virus. Standard transfection protocols known in the art can be used for contacting the Vero cells with the nucleic acids described herein. See e.g. *Current Protocols in Molecular Biology* (F. M. Ausubel et al., eds., 1987, including supplements through 2016). Complementation efficiently can be monitored using any HSV replication efficiency assay known to those in the art, e.g. a plaque forming assay or ELISA assay.

In one embodiment, the method comprises contacting Vero cells with a nucleotide sequence that encodes for a Herpes Simplex virus (HSV) ICP0 protein operably linked to a promoter, wherein the promoter comprises SEQ ID NO:1. In one embodiment, the method comprises contacting Vero cells with a nucleotide sequence that encodes for a Herpes Simplex virus (HSV) ICP0 protein operably linked to a promoter, wherein the promoter comprises SEQ ID NO:2. In one embodiment, the method comprises contacting Vero cells with a nucleotide sequence that encodes for a Herpes Simplex virus (HSV) ICP0 protein that is operably linked to a promoter, wherein the promoter consists essentially of SEQ ID NO: 2. In one embodiment, the HSV ICP0 is HSV-1 ICP0, e.g. SEQ ID NO 5, or variant thereof. In one embodiment, the HSV ICP0 is HSV-2 ICP0, e.g. SEQ ID NO 6, or variant thereof.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Embodiments of the invention are further described in the following numbered paragraphs.

1. A Vero cell line comprising a nucleotide sequence that encodes for a Herpes Simplex virus (HSV) ICP0 protein operably linked to a promoter, wherein the promoter comprises SEQ ID NO:1.
2. The Vero cell line of paragraph 1, wherein the promoter comprises SEQ ID NO: 2.
3. The Vero cell line of any one of paragraphs 1-2, wherein the nucleotide sequence encodes for HSV-1 ICP0 that comprises the amino acid sequence of SEQ ID NO: 5.
4. The Vero cell line of any one of paragraphs 1-3, wherein, the cell line exhibits Vero cell morphology.
5. The Vero cell line of any one of paragraphs 1-4, wherein the cell line is capable of maintaining ICP0 complementation efficiency within 2 standard deviations as measured by a viral replication assay for greater than 20 cell passages.
6. The Vero cell line of any one of paragraphs 1-5, wherein the cell line is capable of maintaining ICP0 complementation efficiency within 2 standard deviations as measured by a viral replication assay for greater than 30 cell passages.
7. The Vero cell line of any one of paragraphs 1-6, wherein the cell line is capable of maintaining ICP0 complementation efficiency within 2 standard deviations as measured by a viral replication assay for greater than 40 cell passages.
8. The Vero cell line of any one of paragraphs 1-7, wherein the nucleotide sequence that encodes for a Herpes Simplex virus (HSV) ICP0 protein operably linked to a promoter comprises SEQ ID NO: 4.
9. The Vero cell line of any one of paragraphs 1-7, wherein the nucleotide sequence that encodes for a Herpes Simplex virus (HSV) ICP0 protein operably linked to a promoter consists essentially of SEQ ID NO: 4.
10. The Vero cell line of any one of paragraphs 1-9, wherein the cell line further comprises an additional nucleic acid that encodes a tetracycline repressor protein (tetR) operably linked to a promoter.
11. The Vero cell line of paragraph 10, wherein the promoter operably linked to the tetracycline repressor protein comprises SEQ ID NO: 9.
12. The Vero cell line of any one of paragraphs 10-11, wherein the nucleic acid that encodes a tetracycline repressor protein encodes the amino acid sequence of SEQ ID NO: 11.
13. The Vero cell line of any one of paragraphs 10-12, wherein the nucleic acid that encodes tetracycline repressor protein (tetR) operably linked to a promoter comprises SEQ ID NO: 7.
14. The Vero cell line of any one of paragraphs 10-12, wherein the nucleic acid that encodes a tetracycline repressor protein (tetR) operably linked to a promoter consists essentially of SEQ ID NO: 7.
15. The Vero cell line of paragraph 9, which is V0-584.
16. The Vero cell line of paragraph 14, which is VOR-124.
17. The Vero cell line of any one of paragraphs 1-16, further comprising a gene encoding antibiotic resistance.
18. The Vero cell line of any one of paragraphs 1-17, further comprising an ICP0 deficient HSV virus.
19. The Vero cell line of any one of paragraphs 1-17, further comprising a nucleic acid encoding a recombinant protein of interest that is operably linked to a promoter.
20. The Vero cell line of paragraph 19, wherein the recombinant protein of interest is a therapeutic protein.
21. The Vero cell line of paragraph 20, wherein the therapeutic protein is a vaccine protein.
22. A method of producing a viral vaccine of interest comprising propagating a virus to be used for vaccination in a Vero cell line of any one of paragraphs 1-21.
23. The method of paragraph 22, wherein the virus to be used for vaccination is an ICP0 deficient HSV virus.
24. The method of paragraph 22, wherein the virus is an adenovirus.
25. A method of producing a recombinant protein of interest comprising propagating the Vero cell line of any one of paragraphs 19-21, for sufficient time to allow for expression of the protein.
26. A method of producing ICP0 deficient HSV virus comprising propagating an HSV ICP0 deficient HSV virus in a Vero cell line of paragraph 1.
27. A method of producing ICP0 deficient HSV virus comprising i) infecting a Vero cell line of any of paragraph 1, with an ICP0 deficient HSV virus, ii) incubating the cell line in a tissue culture medium; and iii) collecting the ICP0 deficient virus produced by the cell line.

All references, publications and patents described herein, in the Examples and throughout the Specification, are incorporated herein by reference in their entirety. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Materials and Methods

Cells: African Green Monkey Kidney CCL-81 (Vero) cells (ATCC) and the human osteosarcoma line U2OS cells were grown and maintained in Dulbecco's Modified Eagle's Medium (DMEM; Sigma Aldrich) supplemented with 10% fetal bovine serum (FBS) in the presence of 100 U/ml penicillin G and 100 µg/ml streptomycin sulfate (GIBCO, Carlsbad, CA) (Yao, et al., *J. Virol.* 69:6249-58 (1995)). U2OS cells are able to complement functionally for the HSV-1 ICP0 deletion (Yao, et al., *J. Virol.* 69:6249-58 (1995)). U2CEP4R11 cells are tetR-expressing U2OS cells that were maintained in DMEM plus 10% FBS and hygromycin B at 50 µg/ml (Yao, et al., *Hum. Gene Ther.* 9:1939-50 (1998)).

Plasmids: pMF3-ICP0 is an HSV-1 ICP0-expressing plasmid that contain no HSV-1 sequence flanking the HSV-1

ICP0 ORF (SEQ ID NO: 3). pMF3-ICP3 encodes ICP0 ORF under the control of modified HCMV minimal promoter consisting of 3 VP16 responsive elements plus 2×CAAAT/SP1 elements 5' to the HCMV TATA element (SEQ ID NO: 4). pcDNA3 and pCDNA4/TO were obtained from Invitrogen (Carlsbad, CA). pcDNA3 encodes neomycin-resistant gene under the control of SV40 promoter. pCDNA4/TO encodes Zeocin-resistant gene. pCDNA4TO-eGFP is an eGFP (enhanced green fluorescent protein)-expressing plasmid.

Plasmid pMF-tetR contains a synthesized DNA fragment consisting of an optimized tetR transcription unit that includes: 1) a modified HCMV major immediate-early promoter that is lack of HCMV promoter sequence from −174 to −370 bp and contains two HSV-1 VP16 responsive elements with the first VP16 responsive element at 149 bp upstream of the HCMV TATA element and the second VP16 responsive element at 274 bp upstream of the HCMV TATA element, 2) beta-globin intron, and 3) a codon optimized tetR coding sequence followed by SV40 poly A signal sequence (SEQ ID NO: 7).

Viruses: N2-lacZ is an HSV-2 ICP0 null mutant, in which the Xho I-ICP0 coding sequence in both copies of the ICP0 gene in the HSV-2 genome are replaced by the Lac Z gene. CJ2-gD2 is an HSV-2 ICP0-deletion mutant-based non-replicating dominant-negative HSV-2 recombinant virus in which both copies of the lacZ gene in N2-lacZ are replaced by DNA sequences encoding the gD2 gene driven by the tetO-bearing HSV-1 major immediate-early ICP4 promoter, while the gene encoding UL9-C535C is under the control of the tetO-containing hCMV major immediate-early promoter in an opposite orientation of the inserted gD2 gene (Akhrameyeva, *J. Virol.* 85:5036-47 (2011)). N2-lacZ was propagated in U2OS cells, while CJ2-gD2 was propagated and plaque assayed in U2CEP4R11 cells.

Example 1: Establishment of an HSV-J ICP0 expressing stable cell line that can complement the plaque forming efficiency of HSV-2 ICP0 null mutant comparable to that of a human osteosacarma cell line, U2OS cells.

We were able to successfully minimize the cytotoxic effect of ICP0 by using a minimal promoter pMF-3 (SEQ ID NO: 01). To establish the ICP0-expressing stable cell lines, we constructed an ICP0-expressing plasmid, pMF3-ICP0. Linearized pMF3-ICP0 plasmid was then transfected into CCL-81 Vero cells along with linearized pcDNA3 by Lipofectamine 2000 (Invitrogen Inc.). At 30 hours post-transfection, cells were seeded into 100 mm dishes at various cell density and were grown in DMEM growth medium containing G418 at 400 ug/ml. G418 resistant colony cells were assayed by its ability to complement the growth of HSV-2 ICP0 null mutant, N2-lacZ, benchmarked against U2OS cells. Among more than 1000 G418-resistant colonies we selected, V0-584 cells represent the only G418-resistant and ICP0-expressing stable cell line that can complement the plaque-formation of N2-lacZ at level comparable to U2OS cells. The results in FIG. 1 show that the plaque-forming efficacy of N2-lacZ in passage 7 V0-584 cells is~2-fold lower than that of U2OS cells and~120-fold higher than that of normal CCL-81 cells. The complementing efficiency of V0-584 cells for N2-lacZ remains 2-3 fold lower than that of U2OS cells at passage 33.

Example 2: Establishment of a tetR- and CPO-expressing Vero cells that can complement the plaque forming efficiency of CJ2-gD2 efficiently.

We have synthesized a DNA sequence at GeneArt (Invitrogen Inc.), which contains an optimized tetR transcription unit that includes: 1) a modified HCMV major immediate-early promoter, which contain the first VP16 responsive element at position 149 bp and the second VP16 responsive element at position 274 bp upstream of the HCMV TATA element, respectively (SEQ ID NO: 9), 2) beta-globin intron (SEQ ID NO: 10), and 3) a codon optimized tetR coding sequence (SEQ ID NO: 8) followed by SV40 poly A signal sequence. The plasmid that contains above mentioned DNA sequence was named pMF-tetR.

To establish tetR- and ICP0-expressing stable CCL-81 Vero cells, V0-584 cells were transfected with linearized pMF-tetR along with linearized pCDNA4/TO (Invitrogen) by Lipofectamine 2000. Transfected cells were then seeded into 100 mm dishes at various cell density and were grown in DMEM growth medium containing G418 at 400 ug/ml and Zeocin at 200 ug/ml. G418—and Zeocin-resistant colony cells were assayed by its ability to complement the growth of CJ2-gD2, benchmarked against U2CEP4R-11 cells. VOR-124 cells represent a G418/Zeocin-resistant stable cell line that can complement the plaque-formation of CJ2-gD2 efficiently even at passage 41. The results in FIG. 2 show that the plaque-forming efficacy of CJ2-gD2 in VOR-124 cells is~4.5-fold lower than that of U2CEP4R-11 cells and is 3,378-fold higher than that of V0-584 cells. The plaque-forming efficiency of N2-lacZ on VOR-124 cells is similar to that of V0-584 cells (data not shown). Notably, VOR-124 cells are morphologically similar to CCL-81 cells and exhibit similar growth kinetics as CCL-81 cells (FIG. 3).

FIG. 4 represents the plaque-forming efficiency of CJ2-gD2 in VOR-124 cells in either the absence or presence of doxycycline. The result shows that the plaque-forming efficiency of CJ2-gD2 in VOR-124 cells in the presence of tetracycline is 2,418-fold lower than in the absence of tetracycline, demonstrating further that like in tetR-expressing Vero cell line, VCEP4R-28 cells (Akhrameyeva, *J. Virol.* 85:5036-47 (2011)), tetR expressed in VOR-124 cells can effectively suppresses the expression of UL9-C535C in CJ2-gD2-infected VOR-124 cells in the absence of doxycycline.

Example 3: Regulation of gene expression from the tetO-containing HCMV major immediate-early promoter in VOR-124 cells.

To further examine the effectiveness of tetR expressed in VOR-124 cells in regulating gene expression from the tetO-containing promoters, VOR-124 cells were seeded into 60 mm dishes at $6\times10^5$ cells/dish. At 21 h post-seeding, cells were transfected with pCDNA4TO-eGFP with Lipofectamine 2000. Transfection medium was removed at 4 h post-transfection followed by addition of normal growth medium with no tetracycline or with doxycycline at a concentration of 0.2 ug/ml. Expression of EGFP was visualized directly under the fluorescence microscopy at 24 h and 48 h post-transfection. As shown in FIG. 5 while a significant number of green cells were seen in VOR-124 cells grown in the presence of doxycycline, a few faint green cells were detected under un-induced conditions, showing that gene expression of the tetO-containing promoter can be tightly regulated by doxycycline in VOR-124 cells.

Moreover, given the intensity of eGFP detected in transfected Vero cells and VOR-124 cells in the presence of tetracycline, the results suggest further that expression of ICP0 in VOR-124 cells can effectively elevate gene expression following transient transfection, consistent with the previously demonstrated potent trans-activating function of ICP0 on gene expression.

SEQUENCE LISTING

SEQ ID NO: 1 Minimal Promoter Sequence in pMF3-ICP0
CCATTGACGCAAATGGGCGGTAGGCGTGTACGGTGGGAGGTCTATATAAG (SEQ ID NO: 1)

SEQ ID NO: 2 Promoter sequence in pMF3-ICP0 (with 3 x VP16 responsive elements
(underlined and highlight) plus 2 x CAAATGGGCGG cis-acting elements (SEQ ID NO: 12))
used for the expression of HSV-1 ICP0 coding sequence.
<u>ATGCTAATGATATACAT</u>GCCACGTACTTATGGTGTC<u>TATGCTAATGATAT</u>TCGCAAATGGGC
GGTAGACCGGTGAATTC<u>ATGCTAATGATAT</u>TCTTTGGTACCATTGACGCAAATGGGCGGTAG
GCGTGTACGGTGGGAGGTCTATATAAG (SEQ ID NO: 2)

SEQ ID NO: 3 HSV-1 ICP0 coding sequence followed by SV40 poly A signal sequence in
plasmids pMF3-ICP0.
ATGGAGCCCCGCCCCGGAGCGAGTACCCGCCGGCCTGAGGGCCGCCCCCAGCGCGAGGTGA
GGGGCCGGGCGCCATGTCTGGGGCGCCATATTGGGGGCGCCATATTGGGGGCGCCATGT
TGGGGGACCCCCGACCCTTACACTGGAACCGGCCGCCATGTTGGGGGACCCCCACTCATAC
ACGGGAGCCGGGCGCCATGTTGGGGCGCCATGTTAGGGGGCGTGGAACCCCGTGACACTAT
ATATACAGGGACCGGGGGCGCCATGTTAGGGGGTGCGGAACCCCCTGACCCTATATATACA
GGGACCGGGGTCGCCCTGTTGGGGGTCGCCATGTGACCCCCTGACTTTATATATACAGACCC
CCAACACATACACATGGCCCCTTTGACTCAGACGCAGGGCCCGGGGTCGCCGTGGGACCCC
CTGACTCATACACAGAGACACGCCCCCACAACAAACACACAAGGACCCGGGGTCGCCGTGTT
GGGGGCGTGGTCCCCACTGACTCATACGCAGGCCCCCCTTACTCACACGCATCTAGGGGGGT
GGGGAGGAGCCGCCCGCCATATTTGGGGGACGCCGTGGGACCCCCGACTCCGGTGCGTCTG
GAGGGCGGGAGAAGAGGGAAGAAGAGGGGTCGGGATCCAAAGGACGGACCCAGACCACCT
TTGGTTGCAGACCCCTTTCTCCCCCCTCTTCCGAGGCCAGCAGGGGGGCAGGACTTTGTGAG
GCGGGGGGGGAGAGGGGGAACTCGTGGGTGCTGATTGACGCGGGAAATCCCCCCCCATTC
TTACCCGCCCCCCTTTTTTCCCCTTAGCCCGCCCCGGATGTCTGGGTGTTTCCCTGCGACCGA
GACCTGCCGGACAGCAGCGACTCTGAGGCGGAGACCGAAGTGGGGGGGCGGGGGGACGCC
GACCACCATGACGACGACTCCGCCTCCGAGGCGGACAGCACGGACACGGAACTGTTCGAGA
CGGGGCTGCTGGGGCCGCAGGGCGTGGATGGGGGGGCGGTCTCGGGGGGGAGCCCCCCCC
GCGAGGAAGACCCCGGCAGTTGCGGGGGCGCCCCCCCTCGAGAGGACGGGGGGAGCGACG
AGGGCGACGTGTGCGCCGTGTGCACGGATGAGATCGCGCCCCACCTGCGCTGCGACACCTT
CCCGTGCATGCACCGCTTCTGCATCCCGTGCATGAAAACCTGGATGCAATTGCGCAACACCT
GCCCGCTGTGCAACGCCAAGCTGGTGTACCTGATAGTGGGCGTGACGCCCAGCGGGTCGTT
CAGCACCATCCCGATCGTGAACGACCCCAGACCCGCATGGAGGCCGAGGAGGCCGTCAGG
GCGGGCACGGCCGTGGACTTTATCTGGACGGGCAATCAGCGGTTCGCCCCGCGGTACCTGA
CCCTGGGGGGGCACACGGTGAGGGCCCTGTCGCCCACCCACCCGGAGCCCACCACGGACGA
GGATGACGACGACCTGGACGACGGTGAGGCGGGGGGCGGCAAGGACCCTGGGGGAGGAGG
AGGAGGAGGGGGGGAGGGAGGAATAGGCGGGCGGGCGAGGAAAGGGCGGGCGGGGA
GGGGGCGTAACCTGATCGCGCCCCCCGTTGTCTCTTGCAGCAGACTACGTACCGCCCGCCCC
CCGCCGGACGCCCCGCGCCCCCCACGCAGAGGCGCCGCCGCGCCCCCCGTGACGGGCGGG
GCGTCTCACGCAGCCCCCAGCCGGCCGCGGCTCGGACAGCGGGCCCCCTCGGCGCCCATCG
GGCCACACGGCAGCAGTAACACCAACACCACCACCAACAGCAGCGGCGGCGGCGGCTCCC
GCCAGTCGCGAGCCGCGGCGCCGCGGGGGCGTCTGGCCCCTCCGGGGGGTTGGGGTTGG
GGTTGGGGTTGTTGAAGCGGAGGCGGGGCGGCCGAGGGGCCGGACGGGCCCCCTTGTCAAC
AGACCCGCCCCCCTTGCAAACAACAGAGACCCCATAGTGATCAGCGACTCCCCCCCGGCCT
CTCCCCACAGGCCCCCGCGGCGCCCATGCCAGGCTCCGCCCCCCGCCCCGGGCCCCCCGCG
TCCGCGGCCGCGTCGGGACCCGCGCGCCCCCGCGCGGCCGTGCCCCGTGCGTGCGAGCGC
CGCCTCCGGGGCCCGGCCCCCGCGCCCCGGCCCCGGGGCGGAGCCGGCCGCCCGCCCCGC
GGACGCGCGCCGTGTGCCCCAGTCGCACTCGTCCCTGGCTCAGGCCGCGAACCAAGAACAG
AGTCTGTGCCGGGCGCGTGCGACGGTGGCGCGCGGCTCGGGGGGGCCGGGCGTGGAGGGTG
GGCACGGGCCCTCCCGCGGCGCCGCCCCCTCCGGCGCCGCCCCGCTCCCCTCCGCCGCCTCT
GTCGAGCAGGAGGCGGCGGTGCGTCCGAGGAAGAGGCGCGGGTCGGGCCAGGAAAACCCC
TCCCCCCAGTCCACGCGTCCCCCCCTCGCGCCGGCAGGGCCAAGAGGGCGACGCACC
CCCCCTCCGACTCAGGGCCGGGGGGGCGCGGCCAGGGTGGGCCCGGGACCCCCCTGACGTC
CTCGGCGGCCTCCGCCTCTTCCTCCTCTGCCTCTTCCTCCTCGGCCCCGACCCCCGCGGGGC
CGCCTCTTCCGCCGCCGGGGCCGCGTCCTCCTCCGCTTCCGCCTCCTCGGGCGGGGCCGTCG
GTGCCCTGGGAGGGAGACAAGAGGAAACCTCCCTCGGCCCCCGCGCTGCTTCTGGGCCGCG
GGGGCCGAGGAAGTGTGCCCGGAAGACGCGCCACGCGGAGACTTCCGGGGCCGTCCCCGC
GGGCGGCCTCACGCGCTACCTGCCCATCTCGGGGGTCTCTAGCGTGGTCGCCCTGTCGCCTTT
ACGTGAACAAGACTATCACGGGGGACTGCCTGCCCATCCTGGACATGGAGACGGGGAACAT
CGGGGCGTACGTGGTCCTGGTGGACCAGACGGGAAACATGGCGACCCGGCTGCGGGCCGCG
GTCCCCGGCTGGAGCCGCCGCACCCTGCTCCCCGAGACCGCGGGTAACCACGTGATGCCCC
CCGAGTACCCGACGGCCCCCGCGTCGGAGTGGAACAGCCTCTGGATGACCCCGTGGGGAA
CATGCTGTTCGACCAGGGCACCCTAGTGGGCGCCCTGGACTTCCGCAGCCTGCGGTCTCGGC
ACCCGTGGTCCGGGGAGCAGGGGCGTCGACCCGGGACGAGGGAAAACAA<u>TAA</u>CAGAACT
TGTTTATTGCAGCTTATAATGGTTACAAATAAAGCAATAGCATCACAAATTTCACAAATAAA
GCATTTTTTTCACTGCATTCTAGTTGTGGTTTGTCCAAACTCATCAATGTATCTTATCATGTCT
GAAGCTTGGC (SEQ ID NO: 3)

SEQ ID NO: 4 2 Promoter sequence in pMF3-ICP0 (with 3 x VP16 responsive elements
(underlined) plus 2 x CAAATGGGCGG cis-acting elements (SEQ ID NO: 12)) used for the
expression of HSV-1 ICP0 coding sequence plus the HSV-1 ICP0 coding sequence.
<u>ATGCTAATGATATACAT</u>GCCACGTACTTATGGTGTC<u>TATGCTAATGATAT</u>TCGCAAATGGGC
GGTAGACCGGTGAATTC<u>ATGCTAATGATAT</u>TCTTTGGTACCATTGACGCAAATGGGCGGTAG
GCGTGTACGGTGGGAGGTCTATATAAGCAGAGCTCGTTTAGTGAACCGTCAGATCGCCTGG
AGACGCCATCCACGCTGTTTTGACCTCCATAGAAGACACCGGGACCGATCCAGCCTCCGCG
GCCGGGAACGGTGCATTGGAACGGACTCTAGAGGATCCATGGAGCCCCGCCCCGGAGCGAG
TACCCGCCGGCCTGAGGGCCGCCCCCAGCGCGAGGTGAGGGGCCGGGCGCCATGTCTGGGG
CGCCATATTGGGGGCGCCATATTGGGGGGCGCCATGTTGGGGGACCCCCGACCCTTACAC

```
                             SEQUENCE LISTING

TGGAACCGGCCGCCATGTTGGGGGACCCCCACTCATACACGGGAGCCGGGCGCCATGTTGG
GGCGCCATGTTAGGGGGCGTGGAACCCCGTGACACTATATATACAGGGACCGGGGGCGCCA
TGTTAGGGGGTGCGGAACCCCCTGACCCTATATATACAGGGACCGGGGTCGCCCTGTTGGG
GGTCGCCATGTGACCCCCTGACTTTATATATACAGACCCCCAACACATACACATGGCCCCTT
TGACTCAGACGCAGGGCCCGGGGTCGCCGTGGGACCCCCTGACTCATACACAGAGACACGC
CCCCACAACAAACACACAAGGACCGGGGTCGCCGTGTTGGGGCGTGGTCCCCACTGACTC
ATACGCAGGCCCCCCTTACTCACACGCATCTAGGGGGGTGGGGAGGAGCCGCCCGCCATAT
TTGGGGGACGCCGTGGGACCCCCGACTCCGGTGCGTCTGGAGGGCGGGAGAAGAGGGAAG
AAGAGGGGTCGGGATCCAAAGGACGGACCCAGACCACCTTTGGTTGCAGACCCCTTTCTCC
CCCCTCTTCCGAGGCCAGCAGGGGGGCAGGACTTTGTGAGGCGGGGGGGGAGAGGGGGA
ACTCGTGGGTGCTGATTGACGCGGGAAATCCCCCCCATTCTTACCCGCCCCCCTTTTTTCCC
CTTAGCCCGCCCCGGATGTCTGGGTGTTTCCCTGCGACCGAGACCTGCCGGACAGCAGCGAC
TCTGAGGCGGAGACCGAAGTGGGGGGGCGGGGGGACGCCGACCACCATGACGACGACTCC
GCCTCCGAGGCGGACAGCACGGACACGGAACTGTTCGAGACGGGGCTGCTGGGGCCGCAG
GGCGTGGATGGGGGGCGGTCTCGGGGGGGAGCCCCCCCGCGGAGGAAGACCCCGGCAGT
TGCGGGGGCGCCCCCCCTCGAGAGGACGGGGGGAGCGACGAGGGCGACGTGTGCGCCGTG
TGCACGGATGAGATCGCGCCCACCTGCGCTGCGACACCTTCCCGTGCATGCACCGCTTCTG
CATCCCGTGCATGAAAACCTGGATGCAATTGCGCAACACCTGCCCGCTGTGCAACGCCAAG
CTGGTGTACCTGATAGTGGGCGTGACGCCCAGCGGGTCGTTCAGCACCATCCCGATCGTGAA
CGACCCCCAGACCCGCATGGAGGCCGAGGAGGCCGTCAGGGCGGGCACGGCCGTGGACTTT
ATCTGGACGGGCAATCAGCGGTTCGCCCCGCGGTACCTGACCCTGGGGGGGCACACGGTGA
GGGCCCTGTCGCCCACCCACCCGGAGCCCACCACGGACGAGGATGACGACGACCTGGACGA
CGGTGAGGCGGGGGGCGGCAAGGACCCTGGGGGAGGAGGAGGAGGAGGGGGGGGAGGG
AGGAATAGGCGGGCGGGCGAGGAAAGGGCGGGCCGGGAGGGGCGTAACCTGATCGCGC
CCCCCGTTGTCTCTTGCAGCAGACTACGTACCGCCCGCCCCCGCCGGACGCCCCGCGCCCC
CCCACGCAGAGGCGCCGCCGCGCCCCCCGTGACGGGCGGGGCGTCTCACGCAGCCCCCCAG
CCGGCCGCGGCTCGGACAGCGCCCCCCTCGGCGCCCATCGGGCCACACGGCAGCAGTAACA
CCAACACCACCACCAACAGCAGCGGCGGCGGCGGCTCCCGCCAGTCGCGAGCCGCAGCGCC
GCGGGGGGCGTCTGGCCCCTCCGGGGGGGTTGGGGTTGGGGTTGGGGTTGTTGAAGCGGAG
GCGGGGCGGCCGAGGGGCCGGACGGGCCCCCTTGTCAACAGACCCGCCCCCCCTTGCAAACA
ACAGAGACCCCATAGTGATCAGCGACTCCCCCCCGGCCTCTCCCCACAGGCCCCCCGCGGC
GCCCATGCCAGGCTCCGCCCCCCGCCCCGGGCCCCCGCGGTCGCCGGCCGCGTCGGGACCC
GCGCGCCCCGCGCGGCCGTGGCCCCGTGCGTGCGAGCGCCGCCTCCGGGGCCCGGCCCCC
GCGCCCCGGCCCCCGGGGCGGAGCCGGCCGCCCGCCCCGCGGACGCGCGCCGTGTGCCCCA
GTCGCACTCGTCCCTGGCTCAGGCCGCGAACCAAGAACAGAGTCTGTGCCGGGCGCGTGCG
ACGGTGGCGCGCGGCTCGGGGGGGCCGGGCGTGGAGGGTGGGCACGGGCCCTCCCGCGGC
GCCGCCCCCTCCGGCGCCGCCCCGCTCCCCTCCGCCGCCTCTGTCGAGCAGGAGGCGGCGGT
GCGTCCGAGGAAGAGGCGCGGGTCGGGCCAGGAAAACCCCTCCCCCCAGTCCACGCGTCCC
CCCCTCGCGCCGGCAGGGGCCAAGAGGGCGGCGACGCACCCCCCCTCCGACTCAGGGCCGG
GGGGGCGCGGCCAGGGTGGGCCGGGACCCCCCTGACGTCCTCGGCGGCCTCCGCCTCTTC
CTCCTCTGCCTCTTCCTCCTCGGCCCCGACCCCCGCGGGGGCCGCCTCTTCCGCCGCCGGGG
CCGCGTCCTCCTCCGCTTCCGCCTCCTCGGGCGGGGCCGTCGGTGCCCTGGGAGGGAGACAA
GAGGAAACCTCCCTCGGCCCCCGCGCTGCTTCTGGGCCGCGGGGGCCGAGGAAGTGTGCCC
GGAAGACGCGCCACGCGGAGACTTCCGGGGCCGTCCCCGCGGGCGGCCTCACGCGCTACCT
GCCCATCTCGGGGGTCTCTAGCGTGGTCGCCCTGTCGCCTTACGTGAACAAGACTATCACGG
GGGACTGCCTGCCCATCCTGGACATGGAGACGGGGAACATCGGGGCGTACGTGGTCCTGGT
GGACCAGACGGGAAACATGGCGACCCGGCTGCGGGCCGCGGTCCCCGGCTGGAGCCGCCG
CACCCTGCTCCCCGAGACCGCGGGTAACCACGTGATGCCCCCGAGTACCCGACGGCCCCC
GCGTCGGAGTGGAACAGCCTCTGGATGACCCCCGTGGGGAACATGCTGTTCGACCAGGGCA
CCCTAGTGGGCGCCCTGGACTTCCGCAGCCTGCGGTCTCGGCACCCGTGGTCCGGGGAGCA
GGGGGCGTCGACCCGGGACGAGGGAAAACAATAA (SEQ ID NO: 4)

SEQ ID NO: 5 HSV-1 ICP0 amino acid sequence
Amino Acid Sequence for HSV-1 ICP0-strain KOS for e.g. variants. See e.g. also: Accession:
P08393.1 GI: 124134; Accession: AFI23590.1 GI: 384597746; Accession: AFI23649.1 GI: 384597805;
Accession: AFE62827.1 GI: 380776964; Accession: AFE62886.1 GI: 380777023; Accession:
ADM22381.1 GI: 304318198; Accession: ALO18731.1 GI: 952947655; Accession: ALO18672.1 GI:
952947596; Accession: ALO18655.1 GI: 952947578; Accession: ALO18596.1 GI: 952947519;
Accession: AKH80472.1 GI: 822581062; Accession: AKH80399.1 GI: 822580988; Accession:
AKG61929.1 GI: 820021112; Accession: AKG61857.1 GI: 820021035; etc. and the like.
MEPRPGASTRRPEGRPQREPAPDVWVFPCDRDLPDSSDSEAETE
VGGRGDADHHDDDSASEADSTDTELFETGLLGPQGVDGGAVSGGSPPREEDPGSCGGA
PPREDGGSDEGDVCAVCTDEIAPHLRCDTFPCMHRFCIPCMKTWMQLRNTCPLCNAKL
VYLIVGVTPSGSFSTIPIVNDPQTRMEAEEAVRAGTAVDFIWTGNQRFAPRYLTLGGH
TVRALSPTHPEPTTDEDDDLDDADYVPPAPRRTPRAPPRRGAAAPPVTGGASHAAPQ
PAAARTAPPSAPIGPHGSSNTNTTTNSSGGGGSRQSRAAVPRGASGPSGGVGVVEAEA
GRPRGRTGPLVNRPAPLANNRDPIVISDSPPASPHRPPAAPMPGSAPRPGPPASAAAS
GPARPRAAVAPCVRAPPPGPGPRAPAPGAEPAARPADARRVPQSHSSLAQAANQEQSL
CRARATVARGSGGPGVEGGHGPSRGAAPSGAAPSGAPPLPSAASVEQEAAVRPRKRRG
SGQENPSPQSTRPPLAPAGAKRAATHPPSDSGPGGRGQGGPGTPLTSSAASASSSSAS
SSSAPTPAGATSSATGAASSSASASSGGAVGALGGRQEETSLGPRAASGPRGPRKCAR
KTRHAETSGAVPAGGLTRYLPISGVSSVVALSPYVNKTITGDCLPILDMETGNIGAYV
VLVDQTGNMATRLRAAVPGWSRRTLLPETAGNHVTPPEYPTAPASEWNSLWMTPVGNM
LFDQGTLVGALDFRSLRSRHPWSGEQGASTRDEGKQ (SEQ ID NO: 5)

SEQ ID NO: 6 HSV-2 ICP0 amino acid sequence ACCESSION YP_009137210
VERSION YP_009137210.1 GI:820945210 [note: for e.g. Variants, see also e.g. Accession:
```

SEQUENCE LISTING

YP_009137151.1 GI: 820945151; Accession: AEV91397.2 GI: 556197555; Accession: AEV91338.2 GI: 556197550;; Accession: ADG01890.1 GI: 295322885;; Accession: ADG01889.1 GI: 295322883; Accession: ADG01888.1 GI: 295322881; Accession: ADG01887.1 GI: 295322879; Accession: ADG01885.1 GI: 295322875; Accession: ADG01886.1 GI: 295322877; etc, and the like]]

```
  1   meprpgtssr adpgperppr qtpgtpaaph awgmlndmqw lassdseeet evgisdddlh 61   rdstseagst dtemfeaglm daatppparpp aerqgsptpa daqgscgggp vgeeeaeagg 121   ggdvcavctd eiapplrcqs fpclhpfcip cmktwiplrn tcplcntpva ylivgvtasg 181   sfstipivnd prtrveaeaa vragtavdfi wtgnqrtapr slslgghtvr alsptppwpg 241   tddedddlad vdyvppaprr aprrggggag atrgtsqpaa trpappgapr ssssggaplr 301   agvgsgsggg pavaavvprv aslppaaggg raqarrvged aaaaegrtpp agqpraaqep 361   pivisdsppp sprrpagpgp lsffssssaq vssgpggggl pqssgraarp raavaprvrs 421   ppraaaapvv sasadaagpa ppavpvdahr aprsrmtqaq tdtqaqslgr agatdargsg 481   gpgaeggpgv prgtntpgaa phaaegaaar prkrrgsdsg paassssasss aaprsplapq 541   gvgakraapr rapdsdsgdr ghgplapasa gaappsasps sqaavaaaas ssssaassss 601   saassssssaa ssssssaasss saasssssss sasssaggag gsvasasgag erretslgpr 661   aaaprgprkc arktrhaegg pepgardpap gltrylpiag vssvvalapy vnktvtgdcl 721   pvldmetghi gayvvlvdqt gnvadllraa apawsrrtll peharncyrp pdyptppase 781   wnslwmtpvg nmlfdqgtlv galdfhglrs rhpwsreqga papagdapag hge
```

SEQ ID NO: 7 Optimized tetR transcription unit: modified HCMV major immediate-early promoter with VP16 responsive elements, beta-globin Intron, codon optimized tetR coding sequence, and SV40 poly A signal sequence.

5'-
GAATTCACGCGTCCGTGCATGC<u>TAATGATATT</u>CCGCCCAACGACCCCCGCCCATTGACGTCA
ATAATGACGTATGTTCCCATAGTAACGCCAATAGGGACTTTCCATTGACGTCAATGGGTGGA
CTATTTACGGTAAACTGCATGC<u>TAATGATATT</u>CTTTGACTCACGGGGATTTCCAAGTCTCCAC
CCCATTGACGTCAATGGGAGTTTGTTTTGGCACCAAAATCAACGGGACTTTCCAAAATGTCG
TAACAACTCCGCCCATTGACGCAAATGGGCGGTAGGCGTGTACGGTGGGAGGTCTA<u>TATA</u>
<u>AG</u>CAGAGCTCGTTTAGTGAACCGTCAGATCGCCTGGAGACGCCATCCACGCTGTTTTGACCT
CCATAGAAGACACCGGGACCGATCCAGCCTCCGTCGCGAGGTGAGTTTGGGGACCCTTGAT
TGTTCTTTCTTTTTCGCTATTGTAAAATTCATGTTATATGGAGGGGGCAAAGTTTTCAGGGTG
TTGTTTAGAATGGGAAGATGTCCCTTGTATCACCATGGACCCTCATGATAATTTTGTTTCTTT
CACTTTCTACTCTGTTGACAACCATTGTCTCCTCTTATTTTCTTTTCATTTTCTGTAACTTTTTC
GTTAAACTTTAGCTTGCATTTGTAACGAATTTTTAAATTCACTTTTGTTTATTTGTCAGATTGT
AAGTACTTTCTCTAATCACTTTTTTTTCAAGGCAATCAGGGTATATTATATTGTACTTCAGCA
CAGTTTTAGAGAACAATTGTTATAATTAAATGATAAGGTAGAATATTTCTGCATATAAATTC
TGGCTGGCGTGGAAATATTCTTATTGGTAGAAACAACTACATCCTGGTCATCATCCTGCCTT
TCTCTTTATGGTTACAATGATATACACTGTTTGAGATGAGGATAAAATACTCTGAGTCCAAA
CCGGGCCCCTCTGCTAACCATGTTCATGCCTTCTTCTTTTTCCTACAGCTGGATCCGTGTTCC
AACCACGGTCACGCTTCGGTGGCCACCATGAGCAGACTGGACAAGAGCAAGGTGATCAACA
GCGCCCTGGAGCTGCTGAACGAGGTGGGCATCGAGGGCCTGACCACCAGAAAGCTGGCCCA
GAAGCTGGGCGTGGAGCAGCCCACCCTGTACTGGCACGTGAAGAACAAGAGAGCCCTGCTG
GACGCCCTGGCCATCGAGATGCTGGACAGACACCACACCCACTTCTGCCCCCTGGAGGGCG
AGAGCTGGCAGGACTTCCTGAGAAACAACGCCAAGAGCTTCAGATGCGCCCTGCTGAGCCA
CAGAGACGGCGCCAAGGTGCACCTGGGCACCAGACCCACCGAGAAGCAGTACGAGACCCT
GGGAGAACCAGCTGGCCTTCCTGTGCCAGCAGGGCTTCAGCCTGGAGAACGCCCTGTACGCC
CTGAGCGCCGTGGGCCACTTCACCCTGGGCTGCGTGCTGGAGGACCAGGAGCACCAGGTGG
CCAAGGAGGAGAGAGAGACCCCCACCACCGACAGCATGCCCCCCCTGCTGAGACAGGCCAT
CGAGCTGTTCGACCACCAGGGCGCCGAGCCCGCCTTCCTGTTCGGCCTGGAGCTGATCATCT
GCGGCCTGGAGAAGCAGCTGAAGTGCGAGAGCGGCAGCTAAATAGGTAGGTAGTCGACCC
GGGACGAGGGAAAACAATAACAGAACTTGTTTATTGCAGCTTATAATGGTTACAAATAAAG
CAATAGCATCACAAATTTCACAAATAAAGCATTTTTTTCACTGCATTCTAGTTGTGGTTTGTC
CAAACTCATCAATGTATCTTATCATGTCTGAAGCTTCTGCAG-3' (SEQ ID NO: 7)

SEQ ID NO: 8 Codon optimized tetR DNA coding sequence plus Kozak consensus sequence
5'-
GCCACCATGAGCAGACTGGACAAGAGCAAGGTGATCAACAGCGCCCTGGAGCTGCTGAACG
AGGTGGGCATCGAGGGCCTGACCACCAGAAAGCTGGCCCAGAAGCTGGGCGTGGAGCAGC
CCACCCTGTACTGGCACGTGAAGAACAAGAGAGCCCTGCTGGACGCCCTGGCCATCGAGAT
GCTGGACAGACACCACACCCACTTCTGCCCCCTGGAGGGCGAGAGCTGGCAGGACTTCCTG
AGAAACAACGCCAAGAGCTTCAGATGCGCCCTGCTGAGCCACAGAGACGGCGCCAAGGTGC
ACCTGGGCACCAGACCCACCGAGAAGCAGTACGAGACCCTGGAGAACCAGCTGGCCTTCCT
GTGCCAGCAGGGCTTCAGCCTGGAGAACGCCCTGTACGCCCTGAGCGCCGTGGGCCACTTC
ACCCTGGGCTGCGTGCTGGAGGACCAGGAGCACCAGGTGGCCAAGGAGGAGAGAGAGACC

```
CCCACCACCGACAGCATGCCCCCCCTGCTGAGACAGGCCATCGAGCTGTTCGACCACCAGG
GCGCCGAGCCCGCCTTCCTGTTCGGCCTGGAGCTGATCATCTGCGGCCTGGAGAAGCAGCTG
AAGTGCGAGAGCGGCAGCTAA (SEQ ID NO: 8)
```

SEQ ID NO: 9 Modified HCMV major immediate-early promoter, which has HCMV promoter sequence from -174 to -370 bp deleted and contains two HSV-1 VP16 responsive elements the first VP16 responsive element at position 149 bp and the second VP16 element at position 274 bp upstream of the HCMV TATA element:
```
5'-
ATGCTAATGATATTCCGCCCAACGACCCCCGCCCATTGACGTCAATAATGACGTATGTTCCC
ATAGTAACGCCAATAGGGACTTTCCATTGACGTCAATGGGTGGACTATTTACGGTAAACTGC
ATGCTAATGATATTCTTTGACTCACGGGGATTTCCAAGTCTCCACCCCATTGACGTCAATGG
GAGTTTGTTTTGGCACCAAAATCAACGGGACTTTCCAAAATGTCGTAACAACTCCGCCCCAT
TGACGCAAATGGGCGGTAGGCGTGTACGGTGGGAGGTCTATATAAGCAGAGCTCGTTTAGT
GAACCGTCAGATCGCCTGGAGACGCCATCCACGCTGTTTTGACCTCCATAGAAGACAC
CGGGACCGAT CCAGCCTCCG (SEQ ID NO: 9)
```

Underlined- VP16 responsive

SEQ ID NO: 10 Beta-globin intron
```
5'-
AGGTGAGTTTGGGGACCCTTGATTGTTCTTTCTTTTTCGCTATTGTAAAATTCATGTTATATG
GAGGGGGCAAAGTTTTCAGGGTGTTGTTTAGAATGGGAAGATGTCCCTTGTATCACCATGGA
CCCTCATGATAATTTTGTTTCTTTCACTTTCTACTCTGTTGACAACCATTGTCTCCTCTTATTT
TCTTTTCATTTTCTGTAACTTTTTCGTTAAACTTTAGCTTGCATTTGTAACGAATTTTTAAATT
CACTTTTGTTTATTTGTCAGATTGTAAGTACTTTCTCTAATCACTTTTTTTTCAAGGCAATCAG
GGTATATTATATTGTACTTCAGCACAGTTTTAGAGAACAATTGTTATAATTAAATGATAAGG
TAGAATATTTCTGCATATAAATTCTGGCTGGCGTGGAAATATTCTTATTGGTAGAAACAACT
ACATCCTGGTCATCATCCTGCCTTTCTCTTTATGGTTACAATGATATACACTGTTTGAGATGA
GGATAAAATACTCTGAGTCCAAACCGGGCCCCTCTGCTAACCATGTTCATGCCTTCTTCTTTT
TCCTACAGCT-3' (SEQ ID NO: 10)
```

SEQ ID NO: 11 Codon optimized tetR DNA coding sequence plus Kozak consensus sequence and 28 bp of ICP27 5' UTR (underlined)
```
GTGTTCCA ACCACGGTCA CGCTTCGGTG GCCACC
ATGAGCAGACTGGACAAGAGCAAGGTGATCAACAGCGCCCTGGAGCTGCTGAACGAGGTG
GGCATCGAGGGCCTGACCACCAGAAAGCTGGCCCAGAAGCTGGGCGTGGAGCAGCCCACC
CTGTACTGGCACGTGAAGAACAAGAGAGCCCTGCTGGACGCCCTGGCCATCGAGATGCTGG
ACAGACACCACACCCACTTCTGCCCCCTGGAGGGCGAGAGCTGGCAGGACTTCCTGAGAAA
CAACGCCAAGAGCTTCAGATGCGCCCTGCTGAGCCACAGAGACGGCGCCAAGGTGCACCTG
GGCACCAGACCCACCGAGAAGCAGTACGAGACCCTGGAGAACCAGCTGGCCTTCCTGTGCC
AGCAGGGCTTCAGCCTGGAGAACGCCCTGTACGCCCTGAGCGCCGTGGGCCACTTCACCCT
GGGCTGCGTGCTGGAGGACCAGGAGCACCAGGTGGCCAAGGAGGAGAGAGAGACCCCCAC
CACCGACAGCATGCCCCCCCTGCTGAGACAGGCCATCGAGCTGTTCGACCACCAGGGCGCC
GAGCCCGCCTTCCTGTTCGGCCTGGAGCTGATCATCTGCGGCCTGGAGAAGCAGCTGAAGTG
CGAGAGCGGCAGCTAA ATAGGTAGGTA (SEQ ID NO: 11)
```

What is claimed is:

1. A Vero cell line comprising a nucleotide sequence that encodes for a Herpes Simplex virus (HSV) ICP0 protein operably linked to a promoter, wherein the promoter comprises SEQ ID NO: 2.

2. The Vero cell line of claim 1, wherein the nucleotide sequence that encodes HSV-1 ICP0 encodes the amino acid sequence of SEQ ID NO: 5.

3. The Vero cell line of claim 1, wherein, the cell line exhibits Vero cell morphology.

4. The Vero cell line of claim 1, wherein the cell line is capable of maintaining ICP0 complementation efficiency within 2 standard deviations as measured by a viral replication assay for greater than 20 cell passages, 30 cell passages, or 40 cell passages.

5. The Vero cell line of claim 1, wherein the cell line further comprises an additional nucleic acid that encodes a tetracycline repressor protein (tetR) operably linked to a promter.

6. The Vero cell line of claim 5, wherein the promoter operably linked to the tetracycline repressor protein comprises SEQ ID NO: 9.

7. The Vero cell line of claim 5, wherein the nucleic acid that encodes a tetracycline repressor protein has the sequence of SEQ ID NO: 11.

8. The Vero cell line of claim 5, wherein the nucleic acid that encodes tetracycline repressor protein (tetR) operably linked to a promoter comprises or consists essentially of SEQ ID NO: 7.

9. The Vero cell line of claim 1, further comprising a gene encoding antibiotic resistance.

10. The Vero cell line of claim 1, further comprising an ICP0 deficient HSV virus.

11. The Vero cell line of claim 1, further comprising a nucleic acid encoding a recombinant protein of interest that is operably linked to a promoter.

12. The Vero cell line of claim 11, wherein the recombinant protein of interest is a therapeutic protein.

13. The Vero cell line of claim 12, wherein the therapeutic protein is a vaccine protein.

14. The Vero cell line of claim 1, wherein the nucleotide sequence comprises or consists essentially of the sequence of SEQ ID NO: 4.

15. A method of producing a viral vaccine of interest comprising propagating a virus to be used for vaccination in a Vero cell line of claim 1.

16. The method of claim 15, wherein the virus to be used for vaccination is an ICP0 deficient HSV virus.

17. The method of claim 15, wherein the virus is an adenovirus.

18. A method of producing ICP0 deficient HSV virus comprising i) infecting a Vero cell line of claim 1, with an ICP0 deficient HSV virus, ii) incubating the cell line in a tissue culture medium; and iii) collecting the ICP0 deficient virus produced by the cell line.

* * * * *